United States Patent [19]
Bradbury et al.

[11] Patent Number: 5,236,937
[45] Date of Patent: Aug. 17, 1993

[54] PYRIDINYL COMPOUNDS WHICH ARE USEFUL AS ANGIOTENSIN II ANTAGONISTS

[75] Inventors: Robert H. Bradbury, Wilmslow; Martin P. Edwards, Bollington; Arnold H. Ratcliffe, Poynton, all of England

[73] Assignee: Imperial Chemical Industries PLC, London, England

[21] Appl. No.: 834,038

[22] Filed: Feb. 11, 1992

[30] Foreign Application Priority Data

| Feb. 11, 1991 | [GB] | United Kingdom | 9102807 |
| May 16, 1991 | [GB] | United Kingdom | 9110593 |
| Jun. 18, 1991 | [GB] | United Kingdom | 9113183 |
| Jul. 29, 1991 | [GB] | United Kingdom | 9116314 |

[51] Int. Cl.$^5$ .................. C07D 401/12; A61K 31/44
[52] U.S. Cl. .................... 514/340; 514/349; 514/350; 514/352; 514/354; 546/276; 546/297; 546/310; 546/312; 546/304; 546/256; 544/315; 544/319; 544/333
[58] Field of Search .......... 546/276, 297, 310, 312, 546/304; 514/340, 349, 350, 352, 354; 544/315, 319, 333

[56] References Cited

U.S. PATENT DOCUMENTS

| 4,820,843 | 4/1989 | Aldrich et al. | 548/252 |
| 4,880,804 | 11/1989 | Carini et al. | 514/234.5 |

FOREIGN PATENT DOCUMENTS

| 0009465 | 9/1979 | European Pat. Off. | 548/252 |
| 0253310 | 1/1988 | European Pat. Off. | 548/252 |
| 0330327 | 2/1989 | European Pat. Off. | 546/212 |
| 0323841 | 7/1989 | European Pat. Off. | 546/276 |
| 0412848 | 2/1991 | European Pat. Off. | 546/330 |
| 0453210 | 4/1991 | European Pat. Off. | 544/123 |
| 0445811 | 9/1991 | European Pat. Off. | 544/123 |
| 0475206 | 3/1992 | European Pat. Off. | 544/123 |
| 0487745 | 6/1992 | European Pat. Off. | 546/276 |
| 0008201 | 6/1991 | France | 546/276 |

OTHER PUBLICATIONS

A. D. Shevchenko, et al., "Synthesis of some p-(aminomethyl)benzoic acid derivatives and their properties" *Chem. Abstr.* (1977), 86, 171.350u.

G. R. Proctor, et al., "Azabenzocycloheptenones. Part XIV. Cyclisation of Amino-acid Derivatives to Tetrahydro-1-benzazepin-5-ones and Tetrahydroquiolin-4-ones" *J. Chem. Soc., Perkin Trans. I* (1972), 1803-1808.

*Primary Examiner*—C. Warren Ivy
*Assistant Examiner*—Zinna N. Davis
*Attorney, Agent, or Firm*—Thomas E. Jackson

[57] ABSTRACT

The invention concerns pharmaceutically useful compounds of the formula I, in which $R^1$, $R^2$, $R^3$, $R^4$, $R^5$, $R^6$, $R^7$, Rz, X and Z have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

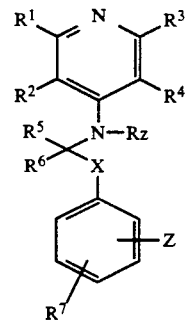

I

11 Claims, No Drawings

PYRIDINYL COMPOUNDS WHICH ARE USEFUL AS ANGIOTENSIN II ANTAGONISTS

This invention concerns novel nitrogen heterocycles and, more particularly, novel nitrogen heterocycles which possess pharmacologically useful properties in antagonizing at least in part one or more of the actions of the substances known as angiotensins, and in particular of that known as angiotensin II (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) on angiotensin I, itself produced by the action of the enzyme renin on the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

In our co-pending European Patent Applications, Publication Nos. 412848 and 453210 there are disclosed certain quinoline and pyridine derivatives respectively which have AII antagonist activity. In European patent Application, Publication No. 330327 there is described ethyl 4-[[(3-amino-4-pyridyl)amino]methyl]benzoate and ethyl 4-[[(3-nitro-4-pyridyl)amino]methyl]benzoate. In European Patent Application, Publication No. 9465 there is described 2-[(4-pyridylamino)methyl]benzoic acid. In Chemical Abstracts, Vol. 86, Abstract No. 171350u there is described 4-[(4-pyridylamino)methyl]benzoic acid.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a heterocyclic compound of the formula I (set out hereinafter, together with the other chemical formulae identified by Roman numerals) wherein $R^1$ is hydrogen, (1–8C)alkyl, (3–8C)cycloalkyl, phenyl or substituted (1–4C)alkyl, the latter containing one or more fluoro substituents or bearing a (3–8C)cycloalkyl, (1–4C)alkoxy or phenyl substituent; $R^2$ is hydrogen, halogeno, (1–8C)alkyl, (3–8C)cycloalkyl, (3–8C)cycloalkyl-(1–4C)alkyl, carboxy, (1–4C)alkoxycarbonyl, (3–6C)alkenyloxycarbonyl, cyano, nitro, phenyl or phenyl(1–4C)alkyl; $R^3$ is selected from halogeno, (1–4C)alkoxy, amino, alkylamino and dialkylamino of up to 6 carbon atoms, and any of the values defined for $R^1$;

$R^4$ is selected from hydrogen, (1–4C)alkyl optionally bearing an amino, hydroxy, (1–4C)alkoxy, carboxy or (1–4C)alkoxycarbonyl substituent or optionally containing one or more fluoro substituents, carboxy, (1–4C)alkoxycarbonyl, (3–6C)alkenyloxycarbonyl, cyano, nitro, carbamoyl, (1–4C)alkanoyl, N-alkylcarbamoyl and di-(N-alkyl)carbamoyl of up to 7 carbon atoms, formyl, halogeno, amino, alkylamino and dialkylamino of up to 6 carbon atoms, (1–4C)alkanoylamino, phenyl, phenyl(1–4C)alkyl and benzoyl, the benzene ring of which last three groups optionally bearing one or two substituents selected from (1–4C)alkyl, (1–4C)alkoxy, halogeno, cyano, trifluoromethyl, nitro, hydroxy, carboxy, (1–4C)alkanoylamino, (1–4C)alkanoyl, fluoro(1–4C)alkoxy, hydroxy(1–4C)alkyl, (1–4C)alkoxy(1–4C)alkyl, carbamoyl, alkyl or dialkylcarbamoyl of up to 7 carbon atoms, sulphamoyl, alkyl or dialkylsulphamoyl of up to 6 carbon atoms, (1–4C)alkoxycarbonyl, (1–4C)alkanesulphonamido, (1–4C)alkyl.S(O)$_n$-[in which n is zero, 1 or 2], 1H-tetrazol-5-yl, phenyl, phenoxy, benzyloxy, benzyloxycarbonyl, benzamido and benzenesulphonamido, the benzene moiety of the last six groups optionally bearing a halogeno, (1–4C)alkyl or (1–4C)alkoxy substituent; or $R^4$ is (1) a group of the formula —$A^1.A^2.B$ wherein $A^1$ is carbonyloxy, $A^2$ is (1–6C)alkylene and B is selected from hydroxy, (1–4C)alkoxy, phenyloxy, phenyl(1–4C)alkoxy, pyridyl(1–4C)alkoxy, 4-morpholino(1–4C)alkoxy, phenylamino, amino, alkylamino and dialkylamino of up to 6 carbon atoms, (1–4C)alkanoylamino, (1–4C)alkylsulphonylamino, phenylsulphonylamino, sulphamoylamino (—NH.SO$_2$.NH$_2$), carboxamidomethylamino (—NH.CH$_2$.CO.NH$_2$), (1–4C)alkanoyloxy, phenylcarbonyloxy, aminocarbonyloxy (—O.CO.NH$_2$), (1–4C)alkylaminocarbonyloxy, carboxy, (1–4C)alkoxycarbonyl, carbamoyl, N-alkylcarbamoyl and di-(N-alkyl)carbamoyl of up to 7 carbon atoms, (1–4C)alkanoyl, 4-morpholino, 1-imidazolyl and succinimido group; or B is a group of the formula —$A^3.B^1$ wherein $A^3$ is oxy, oxycarbonyl or imino and $B^1$ is a 5 or 6-membered saturated or unsaturated heterocyclic ring containing 1 or 2 nitrogen atoms and linked to $A^3$ by a ring carbon atom; or $A^3$ is oxycarbonyl and $B^1$ is a 4-morpholino group or a 5 or 6-membered saturated heterocyclic ring containing 1 or 2 nitrogen atoms, optionally bearing a (1–4C)alkyl group and linked to $A^3$ by a ring nitrogen atom; and wherein $B^1$ the remainder of the ring atoms are carbon; or $R^4$ is (2) a group of the formula —$A^4.B^2$ wherein $A^4$ is (1–6C)alkylene, a carbonyl group or a direct bond and $B^2$ is a 5 or 6-membered saturated or unsaturated heterocylic ring containing a single heteroatom selected from oxygen, sulphur and nitrogen or containing two heteroatoms one of which is nitrogen and the other is oxygen, sulphur or nitrogen, and optionally bearing a (1–4C)alkyl substituent; or $R^3$ and $R^4$ together form an (3–6C)alkenylene group, an (3–6C)alkylene group or an (3–6C)alkylene group in which a methylene is replaced by carbonyl, provided that when $R^3$ and $R^4$ together form one of said latter three groups then $R^2$ is additionally selected from any of the previous values defined for $R^4$; or $R^3$ and $R^4$ together with the carbon atoms to which they are attached complete a benzene, pyridine, pyridazine, pyrimidine or pyrazine ring, which latter five rings may optionally bear one or two substituents independently selected from (1–4C)alkyl, (1–4C)alkoxy, fluoro(1–4C)alkoxy, halogeno, trifluoromethyl, cyano, nitro, hydroxy, amino, alkylamino and dialkylamino of up to 6 carbon atoms, carboxy, (1–4C)alkoxycarbonyl, carbamoyl and N-alkylcarbamoyl and di-(N-alkyl)carbamoyl of up to 7 carbon atoms; or $R^3$ and $R^4$ together form a group of the formula —$(CH_2)_n$—Y—$(CH_2)_m$— wherein n and m are independently selected from zero or the integer 1 to 4 such that the sum of n and m is 2, 3, or 4 and wherein one of the methylene groups may optionally be replaced by a carbonyl group and Y is an oxygen atom, or a group of the formula —S(O)$_p$— or —NR— in which p is zero or the integer 1 or 2, and R is hydrogen, (1–8C)alkyl, (1–8C)alkanoyl, carbamoyl, N-alkylcarbamoyl and di-(N-alkyl)carbamoyl of up to 7 carbon atoms, phenyl, phenyl(1–4C)alkyl or substituted (1–4C)alkyl, the latter containing one or more fluoro substituents; or R is a group of the formula —$A^5$-$A^6.B^3$ wherein $A^5$ is a direct bond or a carbonyl group, $A^6$ is (1–6C)alkylene and $B^3$ is selected from any of the values defined for B or $B^2$;

$R^5$ is hydrogen; $R^6$ is hydrogen or (1–4C)alkyl; $R^7$ is selected from hydrogen, (1–4C)alkyl, (1–4C)alkoxy, halogeno, trifluoromethyl, cyano and nitro; X is phenylene optionally bearing a substituent selected from (1–4C)alkyl, (1–4C)alkoxy, halogeno, (1–4C)alkanoyl, trifluoromethyl, cyano and nitro, or X is a direct bond between the adjacent phenyl group and the carbon atom bearing $R^5$ and $R^6$; Rz is hydrogen, (1–4C)alkyl, (1–4C)alkanoyl or benzoyl; Z is 1H-tetrazol-5-yl, —CO.NH.(1H-tetrazol-5-yl) or a group of the formula —CO.$OR^8$ or —CO.NH.$SO_2.R^9$ in which $R^8$ is hydrogen or a non-toxic, biodegradable residue of a physiologically acceptable alcohol or phenol, and $R^9$ is (1–6C)alkyl, (3–8C)cycloalkyl or phenyl; and wherein any of said phenyl moieties of $R^1$, $R^2$, $R^3$, $R^9$, R, B or $B^3$ may be unsubstituted or bear one or two substituents independently selected from (1–4C)alkyl, (1–4C)alkoxy, halogeno, cyano and trifluoromethyl; or an N-oxide thereof; or a non-toxic salt thereof; but excluding ethyl 4-[[(3-amino-4-pyridyl)amino]methyl]benzoate, ethyl 4-[[(3-nitro-4-pyridyl)amino]methyl]benzoate, 2-[(4-pyridylamino)methyl]benzoic acid and 4-[(4-pyridylamino)methyl]benzoic acid.

It will be appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$, $R^2$ or $R^3$ when it is alkyl is, for example, (1–6C)alkyl such as methyl, ethyl, propyl, butyl, isobutyl, sec-butyl, pentyl or hexyl; and when it is cycloalkyl is, for example, cyclopropyl, cyclopentyl or cyclohexyl.

A particular value for $R^1$ or $R^3$ when it is alkyl containing one or more fluoro substitutents is, for example, fluoromethyl, trifluoromethyl, 2,2,2-trifluoroethyl or pentafluoroethyl; and when it is alkyl bearing a cycloalkyl, (1–4C)alkoxy or phenyl substituent is, for example, cyclopropylmethyl, cyclopentylmethyl, cyclohexylmethyl, 2-methoxyethyl, 2-ethoxyethyl, benzyl, 1-phenylethyl or 2-phenylethyl.

A particular value for $R^2$ when it is cycloalkyl-alkyl is, for example, cyclopropylmethyl, cyclopentylmethyl, cyclohexylmethyl or 2-cyclopentyl-ethyl.

A particular value for $R^2$ or $R^4$ when it is phenylalkyl is, for example, benzyl, 1-phenylethyl or 2-phenylethyl.

A particular value for $R^2$ or $R^4$ when it is alkoxycarbonyl is, for example, methoxycarbonyl, ethoxycarbonyl or propoxycarbonyl; and when it is alkenyloxycarbonyl is, for example, allyloxycarbonyl, 2-methyl-2-propenyloxycarbonyl or 3-methyl-3-butenyloxycarbonyl.

A particular value for $R^6$, $R^7$ or for an optional substituent which may be present when X is phenylene, when it is alkyl is, for example, methyl or ethyl.

A particular value for $R^3$, $R^7$ or for an optional substituent which may be present when X is phenylene, when it is halogeno is, for example, fluoro, chloro, bromo or iodo.

A particular value for $R^3$, $R^7$ or for an optional substituent which may be present when X is phenylene, when it is alkoxy is, for example, methoxy or ethoxy.

A particular value for $R^3$ when it is alkylamino is, for example, methylamino, ethylamino or butylamino; and when it is dialkylamino is, for example, dimethylamino, diethylamino or dipropylamino.

Particular values for $R^4$, or for $R^2$ when it is selected from one of the values for $R^4$, are, by way of example, for alkyl: methyl or ethyl; for halogeno: fluoro, chloro, bromo or iodo; for alkylamino; methylamino, ethylamino or butylamino; for dialkylamino: dimethylamino, diethylamino or dipropylamino; for alkanoylamino: formamido, acetamido or propanamido; for alkanoyl: formyl, acetyl or butyryl; for N-alkylcarbamoyl: N-methyl or N-ethylcarbamoyl; for di(N-alkyl)carbamoyl: N,N-dimethylcarbamoyl or N,N-diethylcarbamoyl; for alkyl bearing an amino, hydroxy, alkoxy, carboxy or alkoxycarbonyl substituent: hydroxymethyl, 1-hydroxyethyl, 2-hydroxyethyl, aminomethyl, 2-aminoethyl, methoxymethyl, 2-methoxyethyl, 2-ethoxyethyl, carboxymethyl, 1-carboxyethyl, 2-carboxyethyl, methoxycarbonylmethyl, ethoxycarbonylmethyl, 2-methoxycarbonylethyl or 2-ethoxycarbonylethyl; and for alkyl containing one or more fluoro substituents: fluoromethyl, trifluoromethyl, 2,2,2-trifluoroethyl or pentafluoroethyl.

Particular values for an optional substituent on $R^4$, or on $R^2$ when it is selected from one of the values for $R^4$, when it is phenyl, phenyl(1–4C)alkyl or benzoyl include, by way of example, for alkyl: methyl and ethyl; for alkoxy: methoxy and ethoxy; and for halogeno: chloro, bromo and iodo; for alkanoylamino: formamido, acetamido and propanamido; for alkanoyl: formyl, acetyl and butyryl; for fluoroalkoxy: trifluoromethoxy, 2-fluoroethoxy, 2,2,2-trifluoroethoxy and 3,3,3-trifluoropropoxy; for hydroxyalkyl: hydroxymethyl, 1-hydroxyethyl and 2-hydroxyethyl; for alkoxyalkyl: 2-methoxyethyl and 2-ethoxyethyl; for N-alkylcarbamoyl: N-methyl and N-ethylcarbamoyl; for di(N-alkyl)carbamoyl: N,N-dimethylcarbamoyl and N,N-diethylcarbamoyl; for N-alkylsulphamoyl: N-methyl and N-ethylsulphamoyl; for di(N-alkylsulphamoyl: N,N-dimethylsulphamoyl and N,N-diethylsulphamoyl; for alkoxycarbonyl: methoxycarbonyl, ethoxycarbonyl and propoxycarbonyl; for alkanesulphonamido: metanesulphonamido and ethanesulphonamido; for alkylthio: methylthio and ethylthio; for alkylsulphinyl; methylsulphinyl and ethylsulphinyl; and for alkylsulphonyl: methylsulphonyl and ethylsulphonyl; and for phenyl, phenoxy, benzyloxy, benzyloxycarbonyl, benzamido and benzenesulphonamido optionally bearing a substituent: phenyl, phenoxy, benzyloxy, benzyloxycarbonyl, benzamido and benzenesulphonamido optionally bearing a fluoro, chloro, bromo, methyl, ethyl, methoxy or ethoxy substituent.

A particular value for $R^3$ and $R^4$ when together they form (3–6C)alkylene is, for example, trimethylene, tetramethylene or pentamethylene; when together they form (3–6C)alkenylene is, for example, 1-propenylene, 2-propenylene, 1-butenylene, 2-butenylene or 3-butenylene; and when together they form (3–6C)alkylene wherein one of the methylene groups is replaced by a carbonyl group is, for example, 1-oxopropylidene, 3-oxopropylidene, 1-oxobutylidene or 4-oxobutylidene.

Particular values for an optional substituent which may be present on $R^3$ and $R^4$ when together with the carbon atoms to which they are attached they complete a benzene, pyridine, pyridazine, pyrimidine or pyrazine ring include, by way of example: for alkyl: methyl and ethyl; for alkoxy: methoxy and ethoxy; for fluoroalkoxy: trifluoromethoxy, 2-fluoroethoxy, 2,2,2-trifluoromethoxy and 3,3,3-trifluoropropoxy; for halogeno:fluoro, chloro, bromo and iodo; for alkylamino: methylamino, ethylamino and butylamino; for dialkylamino: dimethylamino, diethylamino and dipropylamino; for alkoxycarbonyl: methoxycarbonyl and ethoxycarbonyl; for N-alkylcarbamoyl: N-methylcarbamoyl and N-ethylcarbamoyl; and for di-N-alkylcarbamoyl: N,N-dimethylcarbamoyl and N,N-diethylcarbamoyl.

A particular value for $A^2$, $A^4$ or $A^6$ is, for example, methylene, ethylene, trimethylene or tetramethylene, in any of which one methylene may bear 1 or 2 methyl substituents.

A particular value for B or $B^3$ includes, for example, for alkoxy: methoxy, ethoxy and isopropoxy; for phenylalkoxy: benzyloxy and phenethyloxy; for pyridylalkoxy: 2-pyridylmethoxy, 3-pyridylmethoxy, 4-pyridylmethoxy and 3-pyridylethoxy; for 4-morpholinoalkoxy: 4-morpholinomethoxy and 4-morpholinoethoxy; for alkylamino: methylamino, ethylamino and butylamino; for dialkylamino: dimethylamino, diethylamino and dipropylamino; for alkanoylamino: formamido, acetamido and propionylamino; for alkylsulphonylamino: methylsulphonylamino and ethylsulphonylamino; for alkanoyloxy: acetyloxy and propionyloxy; for alkylaminocarbonyloxy: methylaminocarbonyloxy and ethylaminocarbonyloxy; for alkoxycarbonyl: methoxycarbonyl, ethoxycarbonyl and propoxycarbonyl; for N-alkylcarbamoyl: N-methyl and N-ethylcarbamoyl; for di(N-alkyl)carbamoyl: N,N-dimethylcarbamoyl and N,N-diethylcarbamoyl; and for alkanoyl: formyl, acetyl and propionyl.

A particular value for $B^1$ when it is a 5 or 6-membered unsaturated heterocyclic ring containing 1 or 2 nitrogen atoms is, for example, pyrrolyl, imidazolyl, pyrazolyl, pyridyl, pyrazinyl, pyrimidinyl or pyridazinyl; and when it is a 5 or 6-membered saturated heterocyclic ring containing 1 or 2 nitrogen atoms is, for example, pyrrolidinyl, imidazolidinyl, pyrazolinyl, piperidinyl or piperazinyl.

A particular value for an alkyl group which may be present on $B^1$ when it is a 5 or 6-membered saturated heterocyclic ring is, for example, methyl or ethyl.

A particular value for $B^2$ or $B^3$ when it is a 5 or 6-membered saturated or unsaturated heterocyclic ring containing a single hetero atom selected from oxygen, sulphur or nitrogen includes, for example, a thienyl, furyl, pyrrolyl, pyrrolidinyl, pyridyl and piperidyl ring.

A particular value for $B^2$ or $B^3$ when it is a 5 or 6-membered saturated or unsaturated heterocyclic ring containing two heteroatoms one of which is nitrogen and the other is oxygen, sulphur or nitrogen includes, for example, an imidazolyl, imidazolidinyl, pyrazolyl, pyrazolinyl, thiazolyl, thiazolinyl, oxazolyl, oxazolidinyl, pyrimidinyl, pyrazinyl, pyridazinyl, piperazinyl, morpholinyl and thiomorpholinyl ring.

A particular value for an alkyl group which may be present on $B^2$, or on $B^3$ when it is selected from one of the values defined for $B^2$, is, for example, methyl or ethyl.

Particular values for R include, by way of example, for alkyl: methyl, ethyl, propyl, butyl, isobutyl, sec-butyl, pentyl and hexyl; for alkanoyl: formyl, acetyl, propionyl, butyryl, pentanoyl and hexanoyl; for N-alkylcarbamoyl: N-methyl and N-ethylcarbamoyl; for di(N-alkyl)carbamoyl: N,N-dimethylcarbamoyl and N,N-diethylcarbamoyl; for phenylalkyl: benzyl, 1-phenylethyl and 2-phenylethyl; and for alkyl bearing one or more fluoro substitutents: fluoromethyl, trifluoromethyl, 2,2,2-trifluoroethyl and pentafluoroethyl.

A particular value for Rz when it is alkyl is, for example, methyl or ethyl; and when it is alkanoyl is, for example, formyl, acetyl or propionyl.

A particular value for $R^8$ when it is a non-toxic, biodegradable residue of a physiologically acceptable alcohol or phenol is, for example, a residue derived from a (1–6C)alkanol such as methanol or ethanol, or phenol, glycerol or the like.

A particular value for $R^9$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on phenyl moieties of $R^1$, $R^2$, $R^3$, $R^9$, R, B or $B^3$ include, by way of example, for halogeno: fluoro, chloro and bromo; for alkyl: methyl and ethyl; and for alkoxy: methoxy and ethoxy.

A specific value for X which is of particular interest is, for example, p-phenylene.

A preferred value for $R^1$ or $R^3$ is, for example, methyl, ethyl or propyl.

A preferred value for $R^2$ is, for example, hydrogen, alkoxycarbonyl or halogeno (especially iodo or chloro).

A preferred value for $R^4$ is, for example, alkoxycarbonyl, benzoyl or halogeno, especially chloro, bromo or iodo.

A preferred value for $R^3$ and $R^4$ when together they form alkylene is, for example, trimethylene or tetramethylene.

A preferred value for Rz is, for example, hydrogen, methyl or acetyl.

A preferred value for $R^6$, $R^7$ or $R^8$ is, for example, hydrogen.

A preferred value for Z is, for example, 1H-tetrazol-5-yl and which is especially preferred when attached ortho to the group X.

A particularly preferred combination of values is, for example, when $R^1$ and $R^3$ are both alkyl.

A preferred group of compounds of the formula I comprises those compounds of the formula I wherein X is p-phenylene and Z is 1H-tetrazol-5-yl, and wherein $R^1$, $R^2$, $R^3$, $R^4$, $R^5$, $R^6$, $R^7$ and Rz have any of the values defined above, and the non-toxic salts thereof. Especially preferred within this group are those compounds wherein Z is at the ortho position relative to X.

A further preferred group of compounds of the formula I comprises those compounds of the formula I wherein $R^1$ is (1-4C)alkyl; $R^2$ is hydrogen, halogeno or (1-4C)alkoxycarbonyl; $R^3$ is (1-4C)alkyl; $R^4$ is hydrogen, halogeno, (1-4C)alkoxycarbonyl, benzoyl or phenyl, the benzene ring of which last two groups optionally bearing one or two substituents independently selected from (1-4C)alkyl, (1-4C)alkoxy, halogeno, cyano, trifluoromethyl and nitro; $R^5$, $R^6$ and Rz are each hydrogen; X is p-phenylene; and Z is carboxy or 1H-tetrazol-5-yl and is attached at the ortho position relative to X; and the non-toxic salts thereof.

A particularly preferred group of compounds of the formula I comprises those compounds of the formula I wherein $R^1$, $R^2$, $R^3$, $R^5$, $R^7$ and Rz have any of the values defined above, $R^4$ is (1-4C)alkoxycarbonyl or halogeno, $R^6$ is hydrogen, X is p-phenylene and Z is 1H-tetrazol-5-yl, and the non-toxic salts thereof. Especially preferred within this group are those compounds wherein Z is at the ortho position relative to X.

An especially preferred group of compounds of the formula I comprises those compounds of the formula I wherein X is p-phenylene; $R^1$ and $R^3$ are both independently (1-8C)alkyl; $R^2$ is hydrogen; $R^4$ is halogeno; $R^5$, $R^6$, $R^7$ and Rz are all hydrogen; and Z is 1H-tetrazol-5-yl, and the non-toxic salts thereof. Especially preferred within this group are those compounds wherein Z is at the ortho position relative to X.

A particular group of compounds of the invention comprises compounds of the formula Ia wherein q is the integer 1 or 2 and $R^1$, $R^2$, $R^7$, Rz and Z have any of the meanings defined above, and the non-toxic salts thereof. Especially of interest within this group are those compounds wherein the 1H-tetrazol-5-yl ring is at the ortho position relative to the adjacent phenyl ring.

Another particular group of compounds of the invention comprises those compounds of the formula I in which the pyridine ring together with $R^3$ and $R^4$ constitutes a quinoline ring, and the variables $R^1$, $R^2$, $R^5$, $R^6$, $R^7$, Rz, X and Z have any of the meanings defined above.

Further particular groups of compounds of the invention comprise those compounds of the formula I in which the pyridine ring together with $R^3$ and $R^4$ constitutes:

(i) a pyrido-pyridine ring (that is a naphthyridine);
(ii) a pyrido-pyridazine ring;
(iii) a pyrido-pyrazine ring; and
(iv) a pyrido-pyrimidine ring;

wherein each of said groups the variables $R^1$, $R^2$, $R^5$, $R^6$, $R^7$, Rz, X and Z have any of the meanings defined above.

A still further particular group of compounds of the invention comprises compounds of the formula I wherein $R^4$ is (1-4C)alkyl bearing a carboxy or (1-4C)alkoxycarbonyl substituent and $R^1$, $R^2$, $R^3$, $R^5$, $R^6$, $R^7$, Rz, X and Z have any of the meanings defined above.

Compounds of the invention which are of particular interest include, for example, the specific embodiments set out hereinafter in the accompanying Examples. These compounds, or a non-toxic salt thereof, are provided as a further feature of the invention. Of these compounds, those described in Examples 1, 6, 7, 8 and 11, and the non-toxic salts thereof, are particularly preferred.

Although all of the formula I compounds can form salts with suitable acids, it will be appreciated that those compounds of formula I wherein Z is other than an ester group or in which $R^2$ or $R^4$ bear a carboxy group can form salts with bases as well as with acids. Particularly suitable non-toxic salts for such compounds therefore also include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula —CO.OR$^8$ in which R$^8$ is hydrogen), a carboxylic acid derivative of the formula II, in which Q is a protected carboxy group selected from (1-6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1–4C)alkanol, such as aqueous methanol or ethanol. However, it may also be performed in a mixture of an aqueous and non-aqueous solvent such as water and toluene using a conventional quaternary ammonium phase transfer catalyst. The hydrolysis is generally performed at a temperature in the range, for example, 0°–120° C., depending on the reactivity of the group Q. In general, when Q is carbamoyl, temperatures in the range, for example, 40°–120° C. are required to effect the hydrolysis.

Alternatively, when Q is benzyloxycarbonyl the conversion may also be performed by hydrogenolysis, for example using hydrogen at 1-3 bar in the presence of a suitable catalyst, such as palladium on charcoal or on calcium sulphate, in a suitable solvent or diluent such as a (1–4C)alkanol (typically ethanol or 2-propanol) and at a temperature in the range, for example, 0°–40° C.

Further, when Q is t-butoxycarbonyl, the conversion may also be carried out by hydrolysis at a temperature in the range, for example, 0°–100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyltin (for example trimethyltin or tributyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a nitrile of the formula IX with a trialkyltin azide, such as tributyltin azide, or triphenyltin azide respectively. The reaction is conveniently carried out in a suitable solvent or diluent, such as toluene or xylene, and at a temperature in the range, for example, 50°–150° C. Nitriles of the formula IX wherein Rz is hydrogen or alkyl may be obtained, for example, by alkylation of a 4-aminopyridine of the formula IV wherein $R^1$ and $R^3$ are other than hydrogen and Rz is hydrogen or alkyl with a nitrile of the formula X wherein Hal. stands for a suitable leaving group such as chloro, bromo, iodo, methanesulphonyloxy or p-toluenesulphonyloxy, using similar conditions to those used in process (c) described hereinafter. The necessary compounds of formula X may be made by standard procedures such as that illustrated in Scheme 1 for compounds in which X is phenylene. Alternatively, the nitriles of the formula IX may be obtained from stepwise conversion of a compound of formula I wherein Z is a group of the formula —CO.$OR^8$ under standard conditions.

The nitriles of the formula IX wherein Rz is hydrogen or alkyl may also be obtained, for example, by reaction of a pyridine of the formula VII wherein $Y^1$ is a suitable leaving group (such as chloro, bromo, iodo, methanesulphonyl, methanesulphonyloxy, p-toluenesulphonyloxy or trifluoromethanesulphonyloxy) with an amine of the formula XI wherein Rz is hydrogen or alkyl, using similar conditions to those used in process (d) described hereinafter.

A nitrile of formula IX wherein Rz is alkanoyl or benzoyl may subsequently be obtained from a nitrile of the formula IX wherein Rz is hydrogen by acylation using standard conditions well known in the art.

The amines of the formula XI wherein Rz is hydrogen or alkyl may be obtained, for example, by standard procedures such as that illustrated in Scheme 1 for compounds in which X is phenylene, or by analogy with Scheme 2.

Alternatively, compounds of the formula III wherein Rz is hydrogen or alkyl may be obtained, for example, by reaction of a pyridine of the formula VII wherein $Y^1$ is as defined above with an amine of the formula XII wherein Rz is hydrogen or alkyl under similar conditions to those described in process (d) hereinafter. It will be appreciated that a compound of the formula III wherein Rz is alkanoyl or benzoyl may subsequently be obtained from a formula III compound wherein Rz is hydrogen by acylation. The amines of formula XII wherein Rz is hydrogen or alkyl may be obtained, for example, from the appropriate bromomethyl compound by standard procedures such as those shown in Schemes 1 and 2.

c) For compounds of the formula I in which Rz is hydrogen or alkyl, an aminopyridine of the formula IV in which Rz is hydrogen or alkyl is alkylated with a compound of the formula V wherein Hal. stands for a suitable leaving group such as chloro, bromo, iodo, methanesulphonyloxy or p-toluenesulphonyloxy.

The reaction is preferably carried out in the presence of a suitable non-nucleophillic base, for example, an alkali metal tert-butoxide such as sodium or potassium tert-butoxide, an alkali metal hydride such as sodium hydride, or an alkali metal carbonate such as sodium or potassium carbonate, or an organic base such as diisopropylethylamine or 4-dimethylaminopyridine. The reaction is conveniently carried out in a suitable solvent or diluent, for example, a (1–4C)alkanol such as methanol or ethanol, or in a polar solvent such as N,N-dimethylformamide or N-methylpyrrolidone and at a temperature in the range, for example, 10°–100° C. In carrying out process (c), when in the starting material $R^8$ is hydrogen, about two molecular equivalents of a suitable base is generally required, whereas when $R^8$ is other than hydrogen the presence of one molecular equivalent of a suitable base is generally sufficient.

Procedure (c) is particularly suitable for the production of those compounds of the formula I in which Rz is hydrogen or alkyl and Z is a group of the formula —CO.$OR^8$ in which $R^8$ is other than hydrogen, for example wherein $R^8$ is (1–6C)alkyl, benzyl or phenyl, which compounds are also starting materials of formula II for the reaction described in (a) above. Similarly, using an analogous procedure, but starting with the appropriate compound of the formula VI, the starting materials of the formula III may be obtained for procedure (b).

Many of the aminopyridines of formula IV wherein Rz is hydrogen or alkyl are already known and the remainder can be made by analogy therewith using standard procedures of organic chemistry well known in the art, for example as described in standard works of heterocyclic chemistry such as that edited by Elderfield. The necessary compounds of the formula V (and also of formula VI) may be made by standard procedures such as those which are illustrated in Scheme 1 for compounds in which X is phenylene.

Compounds of the formula VI wherein X is phenylene and $R^5$ and $R^6$ are both hydrogen may also be conveniently obtained by reaction of a Grignard reagent, formed from a suitably substituted 4-bromotoluene, with a trialkyltin halide, such as tributyltin chloride, followed by reaction of the resulting (substituted)-phenyltrialkyltin compound with a bromobenzonitrile in the presence of a palladium(O) catalyst, such as tetrakis(triphenylphosphine)palladium, and azo(bisisobutyronitrile). The resultant substituted 4'-methylbiphenylcarbonitrile may then be converted to a compound of the formula VI by carrying out steps (b), (c) and (d) in a similar manner to that shown in Scheme 1. Alternatively, suitably substituted 4'-methylbiphenylcarbonitriles may be obtained by reaction of 4-methylphenylboronic acid with an appropriately substituted bromobenzonitrile in the presence of a suitable palladium catalyst, such as palladium (II)chloride or tetrakis(triphenylphosphine)palladium, and azo(bisisobutyronitrile).

(d) For compounds in which Rz is hydrogen or alkyl, a heterocyclic derivative of the formula VII wherein $Y^1$ is a suitable leaving group (such as chloro, bromo, iodo, methanesulphonyl, methanesulphonyloxy, p-toluenesulphonyloxy or trifluoromethanesulphonyloxy) is reacted with an amine of the formula VIII wherein Rz is hydrogen or alkyl.

The reaction is optionally carried out in the presence of a suitable base, for example an alkali metal carbonate or bicarbonate such as sodium or potassium carbonate or bicarbonate, or an organic base for example a tertiary amine such as triethylamine. The reaction is conveniently carried out in a suitable solvent or diluent, for example a (1–4C)alkanol such as methanol, ethanol or butanol, a non-polar solvent such as dioxane or diphenyl ether, or a polar solvent such as N,N-dimethylformamide or N-methylpyrrolidone, and usually at a temperature in the range of 40° to 180° C.

Heterocyclic derivatives of the formula VII wherein $Y^1$ is halogeno may be obtained, for example, by halogenation of the corresponding 4-pyridones, 4-quinolones and azaquinolones, themselves already known or which can be made by analogy therewith using procedures well known in the art and described in standard works of organic chemistry such as that edited by Elderfield. For example, the formula VII compounds may be obtained by reaction of the corresponding 4-pyridone, 4-quinolone or azaquinolone with phosphorus oxychloride in the absence of a solvent, or in the presence of an inert solvent or diluent such as toluene or dioxane, and at a temperature in the range 60°–110° C. Compounds of the formula VII wherein $Y^1$ is methanesulphonyloxy, p-toluenesulphonyloxy or trifluoromethanesulphonyloxy and $R^1$ and $R^3$ are other than hydrogen may be obtained, for example, by acylation of the corresponding 4-pyridone, 4-quinolone or azaquinolone with the corresponding sulphonyl chloride under standard conditions. Compounds of the formula VII wherein $Y^1$ is methanesulphonyl may be obtained from alkylation of the corresponding mercaptopyridine, mercaptoquinoline or mercaptoazaquinoline, themselves known or obtained by analogy therewith, followed by oxidation under standard conditions. The amines of the formula VIII wherein Rz is hydrogen or alkyl are known or can be prepared by standard procedures well known in the art, for example, as illustrated in, or by analogy with, Schemes 1 and 2.

Certain 4-pyridones are described in *Monatshefte fur Chemie*, 1969, 100, 132; *J. Chem. Soc.* (B), 1968, 866; *Liebigs Ann. Chem.*, 1882, 1656; *Heterocycles*, 1982, 13, 239; and *J. Am. Chem. Soc.*, 1974, 96(4), 1152. Also certain 4-quinolones are described in our copending European patent application, publication no. 412848. Certain 1,5- and 1,7-naphthyridin-4-ones may be obtained by reaction of a suitably substituted 3-aminopyridine with the alkyl ester of an appropriate alkanoylacetic acid in the presence of a suitable acid catalyst (such as p-toluenesulphonic acid) and preferably at ambient temperature, followed by cyclisation of the resulting product by refluxing in a eutectic mixture of 26.5% v/v diphenyl and 73.5% v/v diphenyl oxide. Certain 1,8-naphthyridones are described in *J. Med. Chem.* 1971, 14, 638.

(e) For those compounds of formula I wherein Rz is hydrogen or alkyl and $R^6$ is hydrogen, an aminopyridine of the formula IV wherein Rz is hydrogen or alkyl is reductively alkylated with an aldehyde of the formula XVI.

The reaction may be conveniently carried out in the presence of a suitable reducing agent, such as sodium cyanoborohydride, in a suitable solvent, such as toluene or methanol, and at a temperature in the range, for example, 0° to 50° C. and preferably at or about ambient temperature. Preferably the reaction is carried out in two stages by first dehydrating a mixture of the formula IV and formula XVI compounds, for example by refluxing in a suitable inert solvent (such as toluene) in the presence of a suitable base (such as piperidine). The imine so formed is then reduced, for example with sodium cyanoborohydride in methanol at a temperature in the range 0° to 50° C., and preferably at or about ambient temperature.

The procedure is particularly suitable for the production of those compounds of the formula I in which $R^6$ is hydrogen and Z is a group of the formula —CO.OR$^8$ in which $R^8$ is other than hydrogen, for example wherein $R^8$ is (1–6C)alkyl, benzyl or phenyl, which compounds are also starting materials of formula II for the reaction described in (a) above. Similarly, using an analogous procedure, but starting with the appropriate compound of the formula XVII, starting materials of the formula III wherein $R^6$ is hydrogen may be obtained for procedure (b). Compounds of the formula XVI and XVII may be obtained, for example, as illustrated in Schemes 1 and 2 respectively for compounds in which X is phenylene.

Whereafter, those compounds of formula I wherein Rz is alkanoyl or benzoyl may be obtained by acylation or benzoylation of the corresponding compound of the formula I wherein Rz is hydrogen under standard conditions.

Whereafter, those compounds of formula I wherein Z is 1H-tetrazol-5-yl may be obtained by stepwise conversion of a compound of the formula I wherein Z is a group of the formula —CO.OR$^8$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is —CO.NH.(1H-tetrazol-5-yl), a group of the formula —CO.NH.SO$_2$R$^9$ or a group of the formula —CO.OR$^8$ in which R$^8$ is other than hydrogen, may be obtained, for example, by reacting a carboxylic acid of the formula I in which Z is carboxy (or a reactive derivative of said acid) with 5-aminotetrazole, a sulphonamide of the formula NH$_2$.SO$_2$R$^9$ or a salt thereof (for example, an alkali metal salt), or a hydroxy compound of the formula HO.R$^8$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexycarbodiimide or 3-(3-dimethylaminopropyl)-1-ethylcarbodiimide in the presence of a base such as triethylamine or pyridine. When a reactive derivative is used, either the reaction is carried out in the presence of a base such as mentioned above, or, for the preparation of a compound of the formula I wherein Z is a group of the formula —CO.NH.SO$_2$R$^9$ or a group of the formula —CO.OR$^8$, the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°-60° C.

Whereafter, when an N-oxide derivative of a compound of the formula I is required, a compound of the formula I is oxidised. Suitable oxidising agents include those well known in the art for the conversion of nitrogen heterocycles to their corresponding N-oxide derivatives, for example, hydrogen peroxide or an organic peracid such as m-chloroperbenzoic acid or peracetic acid. The oxidation is preferably carried out in a suitable conventional solvent or diluent for such oxidations, for example dichloromethane, chloroform or acetic acid, and at a temperature in the general range, for example 0° to 80° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure, for example using an aqueous mineral acid such as dilute hydrochloric acid.

According to a further aspect of the invention, there is provided a process for the manufacture of a compound of the formula I wherein Z is tetrazolyl, X is p-phenylene optionally bearing a substituent selected from (1-4C)alkyl, (1-4C)alkoxy, halogeno, trifluoromethyl, cyano and nitro, R$^5$ and R$^6$ are both hydrogen, and R$^1$, R$^2$, R$^3$, R$^4$, R$^7$, and Rz have any of the meanings defined hereinbefore; which comprises reaction of a compound of the formula XIII wherein P$^1$ is an electron-deficient phenyl group or is a pyridyl or pyrimidyl group; R$^{10}$ is hydrogen, (1-4C)alkyl, (1-4C)alkoxy, halogeno, trifluoromethyl, cyano or nitro; and R$^1$, R$^2$, R$^3$, R$^4$, R$^7$ and Rz have any of the values defined above; with a base selected from an alkali metal hydroxide, (1-12C)alkanolate, (1-12C)alkanethiolate, phenolate, thiophenolate or diphenylphosphide, wherein any phenyl ring of the latter three groups may optionally bear a (1-4C)alkyl, (1-4C)alkoxy or halogeno group.

A particular value for P$^1$ when it is an electron-deficient phenyl group includes, for example, a phenyl group bearing 1, 2 or 3 electron-withdrawing groups independently selected from nitro, cyano, trifluoromethyl, di(1-4C)alkylaminosulphonyl (such as dimethylaminosulphonyl or diethylaminosulphonyl) and (1-4C)alkylsulphonyl (such as methylsulphonyl or ethylsulphonyl).

A particular value for R$^{10}$ when it is alkyl is, for example, methyl or ethyl; when it is alkoxy is, for example, methoxy or ethoxy; and when it is halogeno is, for example, fluoro, chloro, bromo or iodo.

A suitable value for a base is, by way of example: for an alkali metal hydroxide: sodium or potassium hydroxide; for an alkali metal alkanolate: an alkali metal (1-8C)alkanolate, for example an alkali metal (1-4C)alkoxide, such as sodium or potassium methoxide, ethoxide, propoxide or butoxide; for an alkali metal alkanethiolate: an alkali metal (1-8C)alkanethiolate, for example an alkali metal (1-4C)alkanethiolate such as sodium or potassium methanethiolate, ethanethiolate, propanethiolate or butanethiolate; for a phenolate or thiophenolate: the sodium or potassium salt of phenol, thiophenol, or a phenol or thiophenol bearing a methyl, ethyl, methoxy, ethoxy, fluoro, chloro, bromo or iodo group.

A particular value for an optional substituent on a phenyl group of an alkali metal phenolate, thiophenolate or diphenylphosphide, when it is alkyl is, for example, methyl or ethyl; when it is alkoxy is, for example, methoxy or ethoxy; and when it is halogeno is, for example, fluoro, chloro or bromo.

A preferred value for P$^1$ is, for example, a nitrophenyl group or a 4-pyridyl, 4-cyanophenyl, 4-dimethylaminosulphonylphenyl, 4-methylsulphonylphenyl or 3-cyano-4-trifluoromethylphenyl group. Of these, 4-nitrophenyl is especially preferred.

A preferred value of X is, for example, when it is unsubstituted p-phenylene.

A particularly preferred base is an alkali metal alkanethiolate such as sodium or potassium propanethiolate, an alkali metal alkanolate such as sodium or potassium ethoxide, or an alkali metal thiophenolate such as sodium or potassium 4-fluorothiophenolate.

It will be appreciated that when the base is an alkali metal alkanolate, alkanethiolate, phenolate, thiophenolate or diphenylphosphide, it may be generated in situ from the corresponding alkanol, alkanethiol, phenol, thiophenol or diphenylphosphine with a suitable alkali metal base such as alkali metal hydride, for example, lithium, potassium or sodium hydride. Alternatively when an alkali metal alkanolate is used, it may be convenient to employ the base as a solution in the corresponding alcohol (for example a solution of sodium methoxide in methanol).

The process of the invention is particularly useful for the preparation of compounds of the formula I wherein the tetrazolyl group is at the ortho position relative to the adjacent phenyl group.

The reaction is conveniently carried out in a suitable inert organic solvent or diluent, for example, a polar solvent such as N,N-dimethylformamide or N-methylpyrrolidone. Alternatively, an alkanol such as methanol or ethanol may be used, for example, when an alkali metal hydroxide or alkoxide such as sodium or potassium hydroxide, methoxide or ethoxide is employed. The reaction is generally carried out at a temperature in the range, for example, $-30°$ C. to $50°$ C. It will be appreciated that the choice of temperature will depend on the nature of the base employed. For example, when an alkali metal alkanethiolate or alkanolate is used, a temperature in the range of $0°$ C. to ambient temperature is preferred.

Compounds of the formula XIII wherein Rz is hydrogen or alkyl may be obtained by reaction of a boronic acid of the formula XIV wherein Rz is hydrogen or alkyl with a compound of the formula XV wherein $P^1$ is an electron-deficient phenyl group having any of the meanings defined above or is a pyridyl or pyrimidyl group, and W is a bromo, iodo or trifluoromethanesulphonyloxy group, in the presence of a palladium(0) catalyst, such as tetrakis(triphenylphosphine)palladium, and azo(bisisobutyronitrile). The reaction is preferably carried out in the presence of a base, such as sodium or potassium carbonate, in an inert solvent or diluent, for example, a hydrocarbon such as toluene or xylene, an ether, such as dioxan or tetrahydrofuran, an (1–4C)alkanol such as methanol or ethanol, water, or mixture thereof, for example a mixture of water, methanol and toluene, and at a temperature in the range of, for example, $50°$ C. to $150°$ C., and conveniently at or about the reflux temperature of the solvent or mixture of solvents used.

Compounds of the formula XIV wherein Rz is hydrogen or alkyl may be obtained, for example, by heating at reflux a 4-methylphenylboronic acid in a solvent such as methyl chloroform with azeotropic removal of water, followed by radical bromination of the product which may be carried out in situ, for example with bromine or N-bromosuccinimide in the presence of azo(bisisobutyronitrile). The resultant 4-bromomethylphenylboronic acid anhydride may then be used to alkylate a compound of the formula IV wherein Rz is hydrogen or alkyl (using similar alkylation conditions to those used in process (c) described above), followed by subsequent acidic hydrolysis, to give a formula XIV compound. Alternatively the product from the alkylation step prior to hydrolysis may be isolated and reacted directly with a compound of the formula XV under similar conditions to those described above to obtain a formula XIII compound directly. In a yet further alternative procedure, a 4-methylphenylboronic acid and an appropriate alkanediol, for example 2,2-dimethylpropan-1,3-diol, may be heated at reflux in a solvent (such as cyclohexane) with azeotropic removal of water followed by free radical bromination of the product, which may be carried out in situ. The resultant bromomethyl compound may then be reacted using analogous procedures to those described above for the 4-bromomethylphenylboronic acid anhydride to obtain a formula XIV compound or a compound of the formula XIII (wherein Rz is hydrogen or alkyl) directly. Compounds of the formula XV may be obtained, for example, as shown in Scheme 3.

It will be appreciated that a compound of the formula XIII wherein Rz is alkanoyl or benzoyl may subsequently be obtained from a formula XIII compound wherein Rz is hydrogen by acylation using standard procedures.

Whereafter, the optional subsequent steps of acylation or benzoylation and/or N-oxide formation and/or non-toxic salt formation and/or formation of an optically active form of a compound of the formula I, may be carried out as described above for procedures (a) to (e).

Certain of the intermediates defined herein are novel, for example the compounds of the formula II, III, IX and XIII, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the renin-angiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The compounds of the invention may also be useful for the treatment of ocular hypertension, glaucoma, cognitive disorders (such as Alzheimer's disease, amnesia, senile dementia and learning disorders), as well as other diseases such as renal failure, cardiac insufficiency, post-myocardial infarction, cerebrovascular disorders, anxiety, depression and certain mental illnesses such as schizophrenia.

The antagonism of one or more of the physiological actions of AII and, in particular, the antagonism of the interaction of AII with the receptors which mediate its effects on a target tissue, may be assessed using one or more of the following, routine laboratory procedures:

Test A: This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, acidic compounds of formula I as defined above show significant inhibition in Test A at a concentration of 50 micromolar or much less.

Test B: This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, acidic compounds of formula I as defined above show significant inhibition in Test B at a final concentration of 50 micromolar or much less. [Note: Compounds of formula I wherein Z is a group of the formula—$CO.OR^8$ in which $R^8$ is other than hydrogen in general show only weak activity in the in vitro Tests A or B.]

Test C: This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D: This in vivo test involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of formula I, the compound of example 1 gave the following results in tests A and C described above:

In test A: an $IC_{50}$ of $3.48 \times 10^{-9}$M;
In test C: an $ED_{50}$ of 0.047 mg/kg (i.v. administration).

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt or N-oxide thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I, or a non-toxic salt thereof, may also be advantageously administered for therapeutic or prophylactic purposes together with another pharmacological agent known in the general art to be of value in treating one or more of the diseases or medical conditions referred to hereinabove, such as a beta-adrenergic blocker (for example atenolol), a calcium channel blocker (for example nifedipine), an angiotensin converting enzyme (ACE) inhibitor (for example lisinopril) or a diuretic (for example furosemide or hydrochlorothiazide). It is to be understood that such combination therapy constitutes a further aspect of the present invention.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following nonlimiting Examples in which, unless otherwise stated:

(i) concentrations and evaporations were carried out by rotary evaporation in vacuo;

(ii) operations were carried out at room temperature, that is in the range 18°–26° C.;

(iii) flash column chromatography was performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) $^1$H NMR spectra were normally determined at 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;

(vi) $^{13}$C NMR spectra were normally determined at 100 MHz in $CDCl_3$ or $d_6$-dimethylsulphoxide ($d_6$-DMSO) using the solvent signal as internal standard, and are expressed as chemical shifts (delta values) in parts per million relative to TMS; and (vii) all end-products had satisfactory microanalyses.

EXAMPLE 1

Concentrated hydrochloric acid (0.5 ml) was added to a suspension of 2,6-dimethyl-3-iodo-4-[(2'-(2-triphenylmethyl-2H-tetrazol-5-yl)biphenyl-4-yl)methylamino]pyridine (A) (215 mg) in dichloromethane/methanol (4 ml) (1:3 v/v) and the mixture stirred for 30 minutes. Volatile material was removed by evaporation and the residue purified by recrystallisation from methanol to give 2,6-dimethyl-3-iodo-4-[(2'-(1H-tetrazol-5-yl)biphenyl-4-yl)methylamino]pyridine hydrochloride as a white solid, m.p. 238°-240° C. (decomposition); NMR ($d_6$-DMSO): 2.4(s,3H), 2.7(s,3H), 4.7(d,2H), 6.6(s,1H), 7.1(d,2H), 7.3(d,2H), 7.4-7.7(m,4H), 8.0(t,1H); mass spectrum (positive fast atom bombardment (+ve FAB), DMSO/nitrobenzyl alcohol): 483$(M+H)^+$; microanalysis, found: C,48.1; H,4.1; N,16.1%; $C_{21}H_{19}N_6I.HCl$ requires: C,48.6; H,3.9; N,16.2%.

The starting material A was prepared as follows:

(i) Benzyltrimethylammonium dichloroiodate (6 g) was added to 4-amino-2,6-dimethylpyridine (2.1 g) and calcium carbonate (2.25 g) in dichloromethane/methanol (55 ml) (8:3 v/v) and the mixture was stirred for 16 hours. Solvent was removed by evaporation and the residue partitioned between 5% sodium metabisulphite solution and dichloromethane. The aqueous phase was separated and washed with dichloromethane. The aqueous phase was then basified with sodium carbonate and extracted with dichloromethane. The organic phase was washed with water, saturated sodium chloride solution and dried ($MgSO_4$). Solvent was removed by evaporation and the residue purified by flash chromatography eluting with dichloromethane/methanol (9:1 v/v) to give 4-amino-2,6-dimethyl-3-iodopyridine (B) (1.7 g) as a light yellow solid, m.p. 103°-110° C.; NMR ($CDCl_3$): 2.3(s,3H), 2.7(s,3H), 4.6(br s,2H), 6.3(s,1H); mass spectrum (chemical ionisation): 249 $(M+H)^+$.

(ii) Compound B (0.4 g) was added to a suspension of sodium hydride (60% dispersion in mineral oil; 77 mg) in DMF (5 ml) and the mixture stirred for 15 minutes. 5-[2-(4'-Bromomethylbiphenylyl)]-2-triphenylmethyl-2H-tetrazole (1.07 g) (obtained as described in European patent application, publication no. 0291969) was added and the mixture stirred at 50° C. for 6 hours and then at ambient temperature for 16 hours. Solvent was removed by evaporation and the residue partitioned between ethyl acetate and water. The organic layer was separated, washed with water, saturated sodium chloride solution and dried ($MgSO_4$). Solvent was removed by evaporation and the residue purified by flash chromatography eluting with dichloromethane/methanol (19:1 v/v) to give 2,6-dimethyl-3-iodo-4-[(2'-(2-triphenylmethyl-2H-tetrazol-5-yl)biphenyl-4-yl)methylamino]pyridine (A) (134 mg), as a viscous yellow oil; NMR ($CDCl_3$): 2.3(s,3H), 2.7(s,3H), 4.3(d,2H), 5.1(t,1H), 6.1(s,1H), 6.9(m,6H), 7.0-7.2(m,4H), 7.2-7.5 (complex m,12H), 7.9(m,1H); mass spectrum (+ve FAB, DMSO/nitrobenzyl alcohol): 725$(M+H)^+$.

EXAMPLES 2-4

Using an analogous procedure to that described in Example 1, but starting from the appropriate compound of formula III wherein L is triphenylmethyl, the following compounds of formula I were obtained in yields of 7-60%.

(EXAMPLE 2): 6,7-Dihydro-3-methoxycarbonyl-2-methyl-4-[(2'-(1H-tetrazol-5-yl)biphenyl-4-yl)methylamino]cyclopenta[b]pyridine hydrochloride as a solid, m.p. 222°-224° C. (decomposition): NMR ($d_6$-DMSO): 1.98-2.17(m,2H), 2.47(s,3H), 2.88-3.05(m,4H), 3.81(s,3H), 4.72(d,2H), 7.05-7.23(m,4H), 7.50-7.74(m,4H), 8.40(t,1H); mass spectrum (+ve FAB, methanol/glycerol): 441$(M+H)^+$; microanalysis, found: C,59.2; H,4.9; N,16.4%; $C_{25}H_{24}N_6O_2.HCl.1.5-H_2O.0.25CH_3CO_2C_2H_5$ requires: C,59.4; H,5.5; N,16.0%.

(EXAMPLE 3): Methyl 2,6-dimethyl-4-[(2'-(1H-tetrazol-5-yl)biphenyl-4-yl)methylamino]pyridine-3-carboxylate hydrochloride as a solid, m.p. 212°-215° C. (decomposition); NMR ($d_6$-DMSO): 2.43(s,3H), 2.59(s,3H), 3.91(s,3H), 4.65(d,2H), 6.87(s,1H), 7.10(d,2H), 7.27(d,2H), 7.53-7.72(m,4H), 8.89(t,1H); mass spectrum (+ve FAB, DMSO/nitrobenzyl alcohol): 415$(M+H)^+$; microanalysis, found: C,60.7; H,5.3; N,18.2%; $C_{23}H_{22}N_6O_2.HCl0.25CH_3CO_2C_2H_5$ requires C,61.0; H,5.3; N, 17.8%.

(EXAMPLE 4): Methyl 2-methyl-6-propyl-4-[(2'(1H-tetrazol-5-yl)-biphenyl-4-yl)methylamino]pyridine-3-carboxylate hydrochloride as an amorphous solid; NMR ($d_6$-DMSO): 0.84(t,3H), 1.57-1.66(m,2H), 2.62(3,3H), 2.70(t,2H), 3.92(s,3H), 4.67(d,2H), 6.81(s,1H), 7.10(d,2H), 7.28(d,2H), 7.49-7.70(m,4H), 8.93(t,1H); mass spectrum (+ve FAB, methanol/nitrobenzyl alcohol): 443$(M+H)^+$; microanalysis, found: C,62.2; H,6.0; N,17.3; Cl,7.2%; $C_{25}H_{26}N_6O_2.HCl$ requires: C,62.7; H,5.6; N,17.6; Cl,7.4%.

The necessary starting materials of formula III used in Examples 2-4, corresponding to starting material A in Example 1, were obtained in yields of 6-20% using an analogous procedure to that described in Example 1, part (ii), as follows:

(EXAMPLE 2A): 6,7-Dihydro-3-methoxycarbonyl-2-methyl-4-[(2'-(2-triphenylmethyl-2H-tetrazol-5-yl)biphenyl-4-yl)methylamino]cyclopenta[b]pyridine; NMR ($CDCl_3$): 1.85-2.07(m,2H), 2.70(s,3H), 2.90-3.08(m,4H), 3.86(s,3H), 4.59(d,2H), 6.91-7.55 (complex m,22H), 7.90-7.94(m,2H).

(EXAMPLE 3A): Methyl 2,6-dimethyl-4-[(2'-(2-triphenylmethyl-2H-tetrazol-5-yl)biphenyl-4-yl)methylamino]pyridine-3-carboxylate; NMR ($CDCl_3$): 2.32(s,3H), 2.67(s,3H), 3.87(s,3H), 4.30(d,2H), 6.24(s,1H), 6.90-6.95(m,6H), 7.03-7.51 (complex m,16H), 7.90-7.95(m,1H), 8.05(t,1H).

(EXAMPLE 4A): Methyl 2-methyl-6-propyl-4-[(2'-(2-triphenylmethyl-2H-tetrazol-5-yl)biphenyl-4-yl)methylamino]pyridine-3-carboxylate; NMR ($CDCl_3$): 0.90(t,3H), 1.59-1.70(m,2H), 2.54(t,2H), 2.66(s,3H), 3.86(s,3H), 4.30(d,2H), 6.23(s,1H), 6.90-6.95(m,6H), 7.03-7.47 (complex m,16H), 7.90-7.94(m,1H), 8.01(t,1H).

The necessary starting materials of formula IV used in Examples 2-4, corresponding to compound B in Example 1 were obtained in yields of 16-52% as follows:

(EXAMPLE 2B): 4-Amino-3-methoxycarbonyl-2-methyl-1,5,6,7-tetrahydrocyclopent[b]pyridine was obtained as described in *Tet. Lett.*, 1990, 3485.

(EXAMPLE 3B): Methyl 4-amino-2,6-dimethylpyridine-3-carboxylate; NMR (CDCl$_3$): 2.36(s,3H), 2.64(s,3H), 3.89(s,3H), 5.84 (broad s,2H), 6.27(s,1H), using an analogous procedure to that described in Example 2B but starting from 3-amino-2-butenenitrile itself obtained as described in *J. Het. Chem.* 1989, 26, 1575.

(EXAMPLE 4B): Methyl 4-amino-2-methyl-6-propylpyridine-3-carboxylate; NMR (CDCl$_3$): 0.95(t,3H), 1.60–1.78(m,2H), 2.56(t,2H), 2.64(s,3H), 3.89(s,3H), 5.80(broad s,2H), 6.25(s,1H), using an analogous procedure to that described in Example 2B but starting from 3-amino-2-hexenenitrile itself obtained as described in European patent no. 129,408.

EXAMPLE 5

2M Sodium hydroxide solution (0.39 ml) was added to a solution of methyl 4'-[(2-methylquinolin-4-ylamino)methyl]biphenyl-2-carboxylate (A) (270 mg) in a mixture of methanol (5 ml) and water (5 ml). The solution was heated under reflux for 30 hours and then diluted with water (20 ml) and ethyl acetate (20 ml). The solid precipitate was collected by filtration and recrystallised from a mixture of methanol and 2M hydrochloric acid to give 4'-[(2-methylquinolin-4-ylamino)methyl]biphenyl-2-carboxylic acid hydrochloride (34 mg), m.p. 198°–200° C.; NMR (d$_6$-DMSO): 2.6(s,3H), 4.7(d,2H), 6.8(s,1H), 7.2–7.8(complex m,9H), 7.9–8.0(d,2H), 8.6(d,1H), 9.75–9.85(br,1H); mass spectrum (electron ionisation (EI)): 368(M+H)$^+$.

The starting material A was obtained as follows:

(i) A 1.6M solution of butyllithium in hexane (24.0 ml) was added dropwise to a stirred solution of 4-bromotoluene (6.0 g) in dry tetrahydrofuran (THF) (50 ml) at −78° C. under an atmosphere of argon. The temperature was maintained at −78° C. for 20 minutes and then a 1M solution of anhydrous zinc chloride in ether (38.6 ml) was added. The solution was kept at −78° C. for 15 minutes, and then tetrakis (triphenylphosphine)palladium (60 mg) in THF (5 ml) was added, followed by methyl-2-iodobenzoate (6.1 g) in THF (10 ml). The solution was allowed to reach ambient temperature over 1 hour, then heated under reflux for 5 hours. The solvent was removed by evaporation and the residue was dissolved in chloroform (150 ml). The solution was washed with a solution of ethylene diaminetetracetic acid (10 g) in water (100 ml) and the aqueous layer was re-extracted with chloroform (100 ml). The combined organic extracts were dried (MgSO$_4$) and the solvent removed by evaporation. The residue was purified by flash chromatography, eluting with ethyl acetate/hexane (1:9 v/v) to give methyl 4'-methylbiphenyl-2-carboxylate (B) as a colourless oil (4.4 g); NMR: 2.4(s,3H), 3.65(s,3H), 7.2(s,4H), 7.35(m,3H), 7.5(m,1H), 7.8(d,1H).

(ii) N-Bromosuccinimide (8.1 g) and azo(bisisobutyronitrile) (130 mg) were added to a solution of compound (B) (9.3 g) in carbon tetrachloride (300 ml). The mixture was heated under reflux for 4 hours and then cooled to ambient temperature. Insoluble material was removed by filtration and the filtrate concentrated. The residue was purified by flash chromatography, eluting with ethyl acetate/hexane (1:9 v/v) to give methyl 4'-(bromomethyl)biphenyl-2-carboxylate (C) as a solid (10.9 g), m.p. 48°–50° C.; NMR: 3.65(s,3H), 4.55(s,2H), 7.25–7.60 complex (m,7H), 7.85(d,1H).

(iii) 2-Nitropropane (7.7 ml) and compound C (20.0 g) were added to a solution of sodium (1.52 ) in ethanol (80 ml) and the solution was heated under reflux for 5 hours. Volatile material was removed by evaporation and the residue was partitioned between ether (300 ml) and water (300 ml). The organic phase was separated, washed with saturated sodium chloride solution and dried (MgSO$_4$). The solvent was removed by evaporation and the residue was purified by flash chromatography, eluting with a mixture of ethyl acetate and hexane (1:9 v/v gradually changing to 1:1 v/v), to give methyl 4'-formylbiphenyl-2-carboxylate (D) (10.2 g) as a waxy solid; NMR (d$_6$-DMSO): 3.6(s,3H), 7.45–7.6(m,4H), 7.7(d of t, 1H), 7.85(d of d, 1H), 7.95(d,2H), 10.05(s,1H).

(iv) A solution of compound D (500 mg), 4-amino-2-methylquinoline (330 mg) and piperidine (50 mg) in toluene was heated at reflux for 20 hours. Volatile material was removed by evaporation and the residue was dissolved in methanol (10 ml). Sodium cyanoborohydride (144 mg) was added and the mixture was stirred for 20 hours. Water (40 ml) was added and the mixture was extracted with ethyl acetate (3×30 ml). The combined extracts were washed with water (30 ml), followed by saturated sodium chloride solution (30 ML) and then dried (MgSO$_4$). The solvent was removed by evaporation and the residue purified by flash chromatography, eluting with a mixture of methanol and dichloromethane (1:9 v/v), to give methyl 4'-[(2-methylquinolin-4-ylamino)methyl]biphenyl-2-carboxylate (A) (280 mg), m.p. 209°–211° C. (after trituration with ether); NMR (d$_6$-DMSO): 2.6(s,3H), 3.6(s,3H), 4.8(d,2H), 6.8(s,1H), 7.3(d,2H), 7.4–7.55(m,4H), 7.6–7.8(m,3H), 7.9–8.0(m,2H), 8.65(d,1H), 9.8(br t,1H).

EXAMPLES 6-7

Using an analogous procedure to that described in Example 1, but starting from the appropriate compound of formula III wherein L is triphenylmethyl, the following compounds of formula I were obtained in yields of 56–75%.

(EXAMPLE 6): 3-Chloro-2,6-dimethyl-4-[(2'-(1H-tetrazol-5-yl)biphenyl-4-yl)methylamino]pyridine hydrochloride as a solid, m.p. 228° C. (decomposition); NMR (d$_6$-DMSO): 2.44(s,3H), 2.57(s,3H), 4.64(d,2H), 6.68(s,1H), 7.08(d,2H), 7.27(d,2H), 7.49–7.73(m,4H), 8.65(t,1H); mass spectrum (+ve FAB, DMSO/methanol/nitrobenzyl alcohol): 391(M+H)$^+$; microanalysis, found: C,58.7; H,4.7; N,19.9; Cl,16.3%; C$_{21}$H$_{19}$ClN$_6$.HCl requires: C,59.0; H,4.7; N,19.7; Cl,16.6%.

(EXAMPLE 7): 2,6-Diethyl-3-iodo-4-[(2'-(1H-tetrazol-5-yl)biphenyl-4-yl)methylamino]pyridine hydrochloride as a white solid, m.p. 248°–250° C. (decomposition); NMR (d$_6$-DMSO): 1.11–1.28(m,6H), 2.70(q,2H), 3.02(q,2H), 4.69(d,2H), 6.54(s,1H), 7.10(d,2H), 7.29(d,2H), 7.49–7.73(m,4H), 8.09(t,1H); mass spectrum (+ve FAB, DMSO/methanol/nitrobenzyl alcohol): 511(M+H)$^+$; microanalysis, found: C,49.4; H,4.3; N,14.8%; C$_{23}$H$_{23}$IN$_6$.HCl.0.5H$_2$O requires: C,49.7; H,4.5; N,15.1%.

The necessary starting materials of formula III used in Examples 6-7, corresponding to starting material A in Example 1, were obtained in yields of 26–31% using an analogous procedure to that described in Example 1, part (ii), as follows:

(EXAMPLE 6A): 3-Chloro-2,6-dimethyl-4-[(2'-(2-triphenylmethyl-2H-tetrazol-5-yl)biphenyl-4-yl)methylamino]pyridine; NMR (CDCl$_3$): 2.36(s,3H), 2.54(s,3H), 4.28(d,2H), 5.02(broad t,1H), 6.25(s,1H), 6.85–6.97(m,6H), 7.01–7.17(m,4H), 7.20–7.55(complex m,12H), 7.95(m,1H); mass spectrum (+ve FAB, methanol/nitrobenzyl alcohol): 633(M+H)+.

(EXAMPLE 7A): 2,6-Diethyl-3-iodo-4-[(2'-(2-triphenylmethyl-2H-tetrazol-5-yl)biphenyl-4-yl)methylamino]pyridine; NMR (CDCl3): 1.15–1.31(m,6H), 2.61(q,2H), 2.97(q,2H), 4.31(d,2H), 5.07(t,1H), 6.09(s,1H), 6.83–7.55(complex m,22H), 7.95(m,1H); mass spectrum (+ve FAB, DMSO/methanol/nitrobenzyl alcohol): 753(M+H)+.

The necessary starting materials of formula IV used in Examples 6–7, corresponding to compound B in Example 1 were obtained as follows:

(EXAMPLE 6B): Chlorine gas (from 6 ml of precondensed chlorine) was passed into a solution of 4-amino-2,6-dimethylpyridine (2 g) in a mixture of concentrated sulphuric acid (20 ml) and water (20 ml) and the mixture was stirred for 1 hour. The mixture was then cooled to 0° C., basified with 4M sodium hydroxide and extracted with ethyl acetate. The organic phase was washed with water, saturated sodium chloride solution and dried. Solvent was removed by evaporation and the residue was purified by flash chromatography eluting with dichloromethane/methanol (9:1 v/v) to give 4-amino-3-chloro-2,6-dimethylpyridine (1.45 g) as an off white solid, m.p. 86° C.; NMR (CDCl3): 2.37(s,3H), 2.52(s,3H), 4.47(s,2H), 6.37(s,1H); mass spectrum (chemical ionisation, ammonia): 157(M+H)+.

(EXAMPLE 7B): 4-Amino-2,6-diethylpyridine (1.8 g) was added to a solution of iodine (3.1 g) and [bis(trifluoroacetoxy)iodo]benzene (5.7 g) in a mixture of dichloromethane (70 ml) and methanol (20 ml) and the mixture was stirred for 16 hours. Solvent was removed by evaporation and the residue was partitioned between ethyl acetate and a mixture of saturated sodium metabisulphite solution (50 ml) and saturated sodium carbonate solution (150 ml). The organic phase was separated, washed with saturated sodium chloride solution and dried. Solvent was removed by evaporation and the residue was purified by flash chromatography eluting with dichloromethane/methanol (97:3 v/v) to give 4-amino-2,6-diethyl-3-iodopyridine (1.33 g) as a solid, m.p. 72°–74° C.; NMR (CDCl3): 1.25(m,6H), 2.65(q,2H), 2.96(q,2H), 4.59(broad s,2H), 6.30(s,1H); mass spectrum (chemical ionisation, ammonia): 277(M+H)+.

The starting material, 4-amino-2,6-diethylpyridine, was prepared as follows:

(i) Methyl 4-amino-2,6-diethylpyridine-3-carboxylate (3.94 g), itself obtained using an analogous procedure to that described in Example 2B but starting from 3-amino-2-pentenenitrile (obtained a described in *J. Het. Chem.*, 1989, 26, 1575) and methyl propionylacetate, was added to a mixture of 2M sodium hydroxide solution (9.5 ml) and methanol (40 ml) and the mixture was heated at reflux for 16 hours. The solution was cooled to ambient temperature and volatile material was removed by evaporation. The residue was partitioned between ethyl acetate and a mixture of 2M hydrochloric acid (9.5 ml) and water (20 ml). The aqueous phase was separated, water was removed by evaporation and the residue was extracted with ethyl acetate/methanol (1:1 v/v). The combined organic extracts were filtered and solvent was removed from the filtrate by evaporation to give 4-amino-2,6-diethylpyridine-3-carboxylic acid (3.46 g) as a yellow-brown foam; NMR (d6-DMSO): 1.18(m,6H), 2.64(q,2H), 3.12(q,2H), 6.49(s,1H), 8.28(broad s,2H),; mass spectrum (chemical ionisation, ammonia): 195(M+H)+.

(ii) 4-Amino-2,6-diethylpyridine-3-carboxylic acid (3.26 g) was heated at 220° C. for 50 minutes. The residue was cooled to ambient temperature and purified by flash chromatography eluting with concentrated aqueous ammonia solution/dichloromethane/methanol (1:85:15 v/v) to give 4-amino-2,6-diethylpyridine (1.94 g) as a solid, m.p. 133°–137° C.; NMR (CDCl3/d6-DMSO): 1.24(t,6H), 2.68(q,4H), 4.48(broad s,2H), 6.27(s,2H); mass spectrum (chemical ionisation, ammonia): 151(M+H)+.

EXAMPLE 8

Using an analogous procedure to that described in Example 1, but starting from the appropriate compound of Formula III wherein L is triphenylmethyl, there was thus obtained 3-chloro-2,6-diethyl-4-[(2'-(1H-tetrazol-5-yl)biphenyl-4-yl)methylamino]pyridine hydrochloride (78% yield) as a solid, m.p. 252°–253° C.; NMR (d6-DMSO): 1.24(m,6H), 2.80(q,2H), 3.0(q,2H), 4.65(d,2H), 6.76(s,1H), 7.07(d,2H), 7.27(d,2H), 7.57(m,4H), 8.65(t,1H); mass spectrum (+ve FAB, DMSO/nitrobenzyl alcohol): 419(M+H)+; microanalysis, found: C,60.1; H,5.5; N,18.2%; $C_{23}H_{23}ClN_6.HCl.0.025H_2O$ requires: C,60.1; H,5.3; N,18.3%.

The necessary starting material of formula III, corresponding to starting material A in Example 1, was obtained using an analogous procedure to that described in Example 1, part (ii), to give 3-chloro-2,6-diethyl-4-[(2'-(2-triphenylmethyl-2H-tetrazol-5-yl)biphenyl-4-yl)methylamino]pyridine (18% yield), as a foam; NMR (CDCl3): 1.25(m,6H), 2.60(q,2H), 2.88(q,2H), 4.28(d,2H), 4.98(t,1H), 6.29(s,1H), 6.92(m,6H), 7.10(m,3H), 7.29(complex m,11H), 7.50(m,2H), 7.98(m,1H): mass spectrum (+ve FAB): 661(M+H)+.

The necessary starting material of formula IV, corresponding to starting material B in Example 1, was obtained using an analogous procedure to that described in Example 6B, but starting from 4-amino-2,6-diethylpyridine obtained as described in Example 7B, to give 4-amino-3-chloro-2,6-diethylpyridine (38% yield), as an oil; NMR (CDCl3): 1.24(m,6H), 2.63(q,2H), 2.89(q,2H), 4.47(broad s,2H), 6.38(s,1H); mass spectrum (chemical ionisation, ammonia): 185(M+H)+.

EXAMPLEs 9-11

Using an analogous procedure to that described in Example 1, but starting from the appropriate compound of formula III wherein L is triphenylmethyl, the following compounds of formula I were obtained in yields of 49–94%:

(Example 9): 2,6-diethyl-3,5-diiodo-4-[(2'-(1H-tetrazol-5-yl)biphenyl-4-yl)methylamino]pyridine hydrochloride as a solid, m.p. 220°–225° C. (decomposition): NMR (d6-DMSO): 1.20(t, 6H), 3.09(q, 4H), 5.0(broad s, 2H), 7.08(d, 2H), 7.24(d, 2H), 7.49–7.77(m, 4H); mass spectrum (-ve FAB, DMSO/methanol/nitrobenzyl alcohol): 635(M-H)−; microanalysis, found: C, 41.3; H, 3.4; N, 12.6%; $C_{23}H_{22}I_2N_6.HCl$ requires: C, 41.1; H, 3.5; N, 12.5%.

(Example 10): 3,5-dichloro-2,6-diethyl-4-[(2'-(1H-tetrazol-5-yl)biphenyl-4-yl)methylamino]pyridine as a solid, m.p. 225°–226° C. (decomposition): NMR (d6-DMSO): 1.21(t, 6H), 2.93(q, H), 5.03(s, 2H), 7.06(d, 2H), 7.20(d, 2H), 7.58(m, 4H), 7.92(broad s, 1H); mass spectrum (+ve FAB, DMSO): 453(M+H)+; microanalysis, found: C, 56.4; H, 4.8; N, 17.1%; $C_{23}H_{22}N_6Cl_2$ requires: C, 56.4; H, 4.7; N, 17.2%.

(Example 11): 3-bromo-2,6-diethyl-4-[(2'-(1H-tetrazol-5-yl)biphenyl-4-yl)methylamino]pyridine hydrochloride as a solid m.p. 258°–259° C. (decomposition): NMR (d$_6$-DMSO): 1.18(t, 3H), 1.24(t, 3H), 2.75(q, 2H), 3.0(q, 2H), 4.68(d, 2H), 6.72(s, 1H), 7.09(d, 2H), 7.29(d, 2H), 7.45°–7.72(m, 4H), 8.49(t, 1H); mass spectrum (+VE FAB, methanol/nitrobenzyl alcohol): 465(M+H)$^+$; microanalysis, found: C, 55.1; H, 4.9; N, 16.7%; $C_{23}H_{23}N_6Br.HCl$ requires: C, 55.3; H, 4.84; N, 16.8%.

The necessary starting materials of formula III used in Examples 9–11, corresponding to compound A in Example 1, were obtained in yields of 35–93% using an analogous procedure to that described in Example 1, part (i), as follows:

(Example 9A): 2,6-diethyl-3,5-diiodo-4-[(2'-(2-triphenylmethyl-2H-tetrazol-5-yl)biphenyl-4-yl)methylamino]pyridine as a solid, m.p. 156°–158° C.; NMR (CDCl$_3$): 1.27(t, 6H), 3.01(q, 4H), 4.20(t, 1H), 4.32(d, 2H), 6.84–6.98(m, 6H), 7.08–7.53(complex m, 16H), 7.96(m, 1H); mass spectrum (+ve FAB, DMSO/nitrobenzyl alcohol): 879(M+H)$^+$.

(Example 10A): 3,5-dichloro-2,6-diethyl-4-[(2'-(2-triphenylmethyl-2H-tetrazol-5-yl)biphenyl-4-yl)methylamino]pyridine as a solid, NMR (CDCl$_3$): 1.26(t, 6H), 2.85(q, 4H), 4.61(d, 2H), 4.7(broad t, 1H), 6.85–7.0(m, 6H), 7.11(s, 4H), 7.15–7.55(complex m, 12H), 7.94(m, 1H); mass spectrum (+ve FAB, methanol): 695(M+H)$^+$.

(Example 11A): 3-bromo-2,6-diethyl-4-[(2'-(2-triphenylmethyl-2H-tetrazol-5-yl)biphenyl-4-yl)methylamino]pyridine as a gum; NMR (d$_6$-DMSO): 1.66(double t, 6H), 2.36(q, 2H), 2.78(q, 2H), 4.4(d, 2H), 6.17(s, 1H), 6.45(t, 1H), 6.88(m, 6H), 7.02(d, 2H), 7.19(d, 2H), 7.24–7.4(complex m, 8H), 7.43(dd, 1H), 7.55(m, 2H), 7.76(dd, 1H); mass spectrum (+ve FAB, DMSO/methanol/nitrobenzyl alcohol): 704,706(M+H)$^+$.

The necessary starting materials of formula IV used in Examples 9–11, corresponding to compound B in Example 1 were obtained as follows:

(Example 9B): 4-amino-2,6-diethyl-3,5-diiodopyridine as a solid, m.p. 72°–74° C.; NMR (CDCl$_3$): 1.25(t, 6H), 2.95(q, 4H), 5.25(broad s, 2H); mass spectrum (chemical ionisation, ammonia): 277(M+H)$^+$, using an analogous procedure to that described in Example 7B but using twice the amount of [bis(trifluoroacetoxy)iodo]benzene.

(Example 10B): 4-amino-3,5-dichloro-2,6-diethylpyridine as a solid, m.p. 83°–85° C.; NMR (CDCl$_3$): 1.25(t, 6H), 2.84(q, 4H), 4.89(broad s, 2H); mass spectrum (chemical ionisation, ammonia): 219,221,223(M+H)$^+$, using an analogous procedure to that described in Example 6B but using twice the volume of chlorine.

(Example 11B): N-Bromosuccinimide (2.3 g) was added to a solution of 4-amino-2,6-diethylpyridine (2 g) in 1,4-dioxan (10 ml) and methanol (5 ml) and the mixture was stirred for 16 hours. Solvent was removed by evaporation and the residue was partitioned between ethyl acetate (80 ml) and 0.1M acetic acid solution (75 ml). The organic phase was separated and washed with 0.1M acetic acid (75 ml). The combined aqueous extracts were basified to pH 10 with sodium hydroxide solution and re-extracted with ethyl acetate (2×50 ml). The organic extracts were washed with saturated sodium chloride solution and dried (MgSO$_4$). The solvent was removed by evaporation to give 4-amino-3-bromo-2,6-diethylpyridine (B) (600 mg) as an oil; NMR (d$_6$-DMSO): 1.15(t, 6H), 2.49(q, 2H), 2.72(q, 2H), 5.95(broad s, 2H), 6.38(s, 1H).

EXAMPLE 12

Concentrated hydrochloric acid (0.4 ml) was added to a suspension of 3-chloro-2,6-diethyl-4-[N-(2'-(2-triphenylmethyl-2H-tetrazol-5-yl)biphenyl-4-yl)methyl-N-methylamino]pyridine (A) (220 mg) in methanol (5 ml) and the mixture was stirred for 6 hours. Volatile material was removed by evaporation and the residue partitioned between ether and sodium carbonate solution. The aqueous layer was separated, acidified to pH 6 with 4M hydrochloric acid and extracted with dichloromethane (3×25 ml). The combined organic extracts were dried and solvent removed by evaporation. The residue was purified by flash chromatography eluting with dichloromethane/methanol (9:1 v/v) to give 3-chloro-2,6-diethyl-4-[N-(2'-(1H-tetrazol-5-yl)biphenyl-4-yl)methyl-N-methylamino]pyridine as a solid, m.p. 110° C. (decomposition); NMR (d$_6$-DMSO): 1.1(d, of t, 6H), 2.64(q, 2H), 2.74(s, 3H), 2.84(q, 2H), 4.37(s, 2H), 6.81(s, 1H), 7.07(d, 2H), 7.27(d, 2H), 7.6(m, 4H); mass spectrum (+ve FAB, DMSO): 432,434(M+H)$^+$; microanalysis, found: C, 64.6; H, 6.0; N, 17.9%; $C_{24}H_{25}N_6Cl.0.75H_2O.0.125C_4H_{10}O$ requires: C, 64.4; H, 5.9; N, 18.4%.

The starting material A was prepared as follows:

3-Chloro-2,6-diethyl-4-[(2'-(2-triphenylmethyl-2H-tetrazol-5-yl)biphenyl-4-yl)methylamino]pyridine (335 mg) was added to a mixture of potassium t-butoxide (75 mg) and 1,4,7,10,13,16-hexaoxacyclooctadecane (10 mg) in THF (10 ml) and the mixture was stirred for 15 minutes. Iodomethane (0.04 ml) was added and the solution heated at reflux for 6 hours. The mixture was cooled to ambient temperature and solvent was removed by evaporation. The residue was purified by flash chromatography eluting with ethyl acetate/hexane (1:1 v/v) to give 3-chloro-2,6-diethyl-4-[N-(2'-(2-triphenylmethyl-2H-tetrazol-5-yl)biphenyl-4-yl)methyl-N-methylamino]-pyridine (A) (220 mg) as a foam; NMR (CDCl$_3$): 1.28(double t, 6H), 2.60(s, 3H), 2.72(q, 2H), 2.96(q, 2H), 4.24(s, 2H), 6.59(s, 1H), 6.89(m, 6H), 7.13(m, 3H), 7.30(complex m, 14H), 7.95(m, 1H).

EXAMPLE 13

4M Hydrochloric acid (1.5 ml) was added to a solution of 2,6-diethyl-4-[N-acetyl-N-(2'-(2-triphenylmethyl-2H-tetrazol-5-yl)biphenyl-4-yl)methylamino]pyridine (A) (0.67 g) in 1,4-dioxan (10 ml) and the mixture was stirred for 4 hours. Volatile material was removed by evaporation and the residue purified by flash chromatography eluting with dichloromethane/methanol (17:3 v/v) to give 2,6-diethyl-4-[N-acetyl-N-(2'-(1H-tetrazol-5-yl)biphenyl-4yl)methylamino]pyridine as a solid; NMR (d$_6$-DMSO): 1.17(t, 6H), 1.97(t, 3H), 2.67(q, 4H), 4.89(s, 2H), 6.95(s, 2H), 7.05(q, 4H), 7.55(m, 4H); mass spectrum (+ve FAB, benzyl alcohol/methanol): 449(M+Na)$^+$, 427(M+H)$^+$; microanalysis, found: C, 67.8; H, 6.4; N, 18.5%; $C_{25}H_{26}N_6O.0.125C_4H_{10}O$ requires: C, 67.5; H, 6.5; N, 18.9%.

The starting material A was prepared as follows:

(i) N-acetylimidazole (0.61 g) was added to a solution of 4-amino-2,6-diethylpyridine (0.61 g) in toluene (10 ml) and the mixture was heated at reflux for 16 hours. The mixture was cooled to ambient temperature and solvent was removed by evaporation. The residue was purified by flash chromatography eluting with ethyl acetate to give 4-(N-acetylamino)-2,6-diethylpyridine (B) (0.66 g) as a solid, m.p. 74°–78° C.; NMR (CDCl₃): 1.26(t, 6H), 2.18(s, 3H), 2.74(q, 4H), 7.18(s, 2H), 7.75(broad s, 1H); mass spectrum (chemical ionisation, ammonia): 193(M+H)⁺.

(ii) Sodium hydride (60% dispersion in mineral oil; 88 mg) was added to a solution of 4-(N-acetylamino)-2,6-diethylpyridine (B) (0.3 g) in DMF (10 ml) and the mixture was stirred for 30 minutes. 5-[2-(4'-Bromomethylbiphenylyl)]-2-triphenylmethyl-2H-tetrazole (1.32 g) was added and the mixture was stirred for 2 hours. Solvent was removed by evaporation and the residue was partitioned between ethyl acetate (50 ml) and 0.5M sodium carbonate solution (50 ml). The organic phase was separated and the aqueous phase was extracted with ethyl acetate (2×25 ml). The combined organic phases were washed with saturated sodium chloride solution, dried (MgSO₄) and solvent was removed by evaporation. The residue was purified by flash chromatography eluting with ethyl acetate/toluene (2:3 v/v) to give 2,6-diethyl-4-[N-acetyl-N-(2'-(2-triphenylmethyl-2H-tetrazol-5-yl)biphenyl-4-yl)methylamino]pyridine as a solid, m.p. 98°–102° C.; NMR (CDCl₃): 1.21(t, 3H), 1.96(s, 3H), 2.7(q, 2H), 4.8(s, 2H), 6.6(s, 2H), 6.8–7.1(m, 10H), 7.15–7.4(complex m, 10H), 7.45(m, 2H), 7.9(dd, 1H); mass spectrum (+ve FAB, DMSO/nitrobenzyl alcohol): 691(M+Na)⁺, 669(M+H)⁺.

EXAMPLE 14

Using an analogous procedure to that described in Example 12, but starting from the appropriate compound of formula III, wherein L is triphenylmethyl, there was thus obtained 3-benzoyl-6-ethyl-2-methyl-4-[(2'-(1H-tetrazol-5-yl)biphenyl-4-yl)methylamino]pyridine hydrochloride as a solid (26% yield), m.p. 214°–217° C.; NMR (d₆-DMSO): 1.24(t, 3H), 2.19(s, 3H), 2.77(q, 2H), 4.51(d, 2H), 6.82(s, 1H), 7.05(d, 2H), 7.15(d, 2H), 7.5–7.9(complex m, 9H), 8.31(t, 1H); mass spectrum (+ve FAB, methanol/nitro-benzyl alcohol): 475(M+H); microanalysis, found: C, 67.1, H, 5.3, N, 16.3%; C₂₉H₂₆N₆O.HCl.0.2C₂H₅OH.0.5H₂O requires: C, 66.7; H, 5.1; N, 15.9%.

The necessary starting material of formula III corresponding to starting material A in Example 12 was obtained in a yield of 19% using an analogous procedure to that described in Example 12 as follows:

(Example 14A): 3-benzoyl-6-ethyl-2-methyl-[(2'-(2-triphenylmethyl-2H-tetrazol-5-yl)biphenyl-4-yl)methylamino]pyridine as a foam; NMR (d₆-DMSO): 1.06(t, 3H), 1.99(s, 3H), 2.45(q, 2H), 4.26(d, 2H), 6.27(s, 1H), 6.45(t, 1H), 6.75–6.9(m, 7H), 6.98(d, 2H), 7.08(d, 2H), 7.15–7.40(complex m, 9H), 7.40–7.70(complex m, 6H), 7.75(m, 2H); mass spectrum (+ve FAB, methanol/nitrobenzyl alcohol): 717(M+H)⁺.

The necessary starting material of formula IV corresponding to compound B in Example 1 was obtained as follows:

(i) A mixture of 3-amino-1-phenyl-2-buten-1-one (2.3 g) and 5-(1-hydroxypropylidene)-2,2-dimethyl-1,3-dioxane-4,6-dione (4.0 g) was heated at 120° C. for 1 hour. The mixture was cooled to ambient temperature and the residue was purified by flash chromatography eluting with dichloromethane/methanol (19:1 v/v) to give 3-benzoyl-1,4-dihydro-6-ethyl-2-methyl-4-oxopyridine (C) (0.15 g) as a solid, m.p. 203° C.; NMR (d₆-DMSO): 1.2(t, 3H), 2.07(s, 3H), 2.5(q, 2H), 5.96(s, 1H), 7.44–7.50(m, 2H), 7.57–7.60(m, 1H), 7.72–7.76(m, 2H), 11.3(broad s, 1H); mass spectrum (chemical ionisation, ammonia): 242(M+H)⁺.

(ii) 4-Methylphenylsulphonyl isocyanate (0.66 ml) was added to a stirred suspension of compound C (0.48 g) in acetonitrile and the mixture was heated at reflux for 2.5 hours. The mixture was cooled to ambient temperature and the product was collected by filtration to give 3-benzoyl-6-ethyl-2-methyl-4-[(4-methylphenylsulphonyl)amino]pyridine (D) (0.65 g) as a solid, m.p. 244°–246° C.; NMR (d₆-DMSO): 1.19(t, 3H), 2.13(s, 3H), 2.31(s, 3H), 2.65(q, 2H), 7.08(s, 1H), 7.15(d, 2H), 7.32(d, 2H), 7.50–7.68(m, 5H), 12.63(s, 1H); mass spectrum (+ve FAB, glycerol/methanol): 395(M+H)⁺.

(iii) A solution of compound D (0.64 g) in concentrated sulphuric acid (3 ml) was heated at 50° C. for 1 hour. The solution was cooled to ambient temperature and added cautiously to crushed ice. The mixture was basified to pH 9 with solid sodium carbonate and the precipitate was collected by filtration to give 4-amino-3-benzoyl-6-ethyl-2-methylpyridine (B) (0.35 g) as a solid, m.p. 149°–151° C.; NMR (d₆-DMSO): 1.19(t, 3H), 1.97(s, 3H), 2.53(q, 2H), 5.78(s, 2H), 6.40(s, 1H), 7.49–7.73(m, 5H); mass spectrum (chemical ionisation, ammonia): 241(M+H)⁺.

EXAMPLE 15

A solution of sodium methoxide in methanol (0.5 ml, 30% w/v) was added to a solution of 2,6-diethyl-3-(4-methylphenyl)-4-[(2'-(1-(4-nitrophenyl)-1H-tetrazol-5-yl)biphenyl-4-yl)methylamino]pyridine (A) (90 mg) in methanol (10 ml) and the mixture was heated at reflux for 48 hours. Volatile material was removed by evaporation and the residue was dissolved in water (10 ml). The solution was acidified to pH 5 with 1M citric acid solution. The product was collected by filtration and purified by flash chromatography eluting with dichloromethane/methanol (3:17 v/v) to give 2,6-diethyl-3-(4-methylphenyl)-4-[(2'-(1H-tetrazol-5-yl)biphenyl-4-yl)methylamino]pyridine (31 mg) as a solid; NMR (d₆-DMSO): 1.02(t, 3H), 1.20(t, 3H), 2.41(s, 3H), 2.5(q, 2H), 2.73(q, 2H), 4.48(d, 2H), 6.65(s, 1H), 7.05(d, 2H), 7.20(m, 5H), 7.55(m, 6H).

The starting material A was prepared as follows:

(i) Thionyl chloride (120.5 g) was added to a stirred mixture of 2-bromobenzoic acid (194 g) in toluene (500 ml) and N,N-dimethylformamide (DMF) (5 ml) and the mixture heated at 80° C. for 4 hours. The solution was cooled to 20° C. and added slowly to a solution of 4-nitroaniline (133.1 g) in toluene (500 ml) and N-methylpyrrolidone (NMP) (120 ml), maintaining the temperature of the reaction mixture between 20°–25° C. The reaction mixture was then stirred for 24 hours when a solid precipitated. Water (360 ml) was added with rigorous stirring and the suspended solid collected by filtration, and washed successively with water, toluene and acetonitrile to give 2-bromo-N-(4-nitrophenyl)benzamide (B) as a solid, in 87% yield; m.p. 200°–202° C.; NMR (d₆-DMSO): 7.4–7.8(m, 7H), 8.0(d, 2H), 8.3(d, 2H), 11.5(brs, 1H); which was used without further purification.

(ii) Triethylamine (1.04 g; 10.38 mmol) was added to a mixture of amide B (3 g; 9.35 mmol) in acetonitrile (12 ml) and DMF (0.189 g; 2.58 mmol) and the mixture was stirred for 90 minutes. Thionyl chloride (1.44 g; 12.14 mmol) was then added slowly keeping the reaction temperature below 25° C. The mixture was stirred for 5 hours at ambient temperature and then cooled to 10° C. Triethylamine (2.83 g; 28 mmol) was then added, followed by sodium azide (1.33 g; 20.4 mmol) and tetrabutylammonium bromide (0.42 g; 1.3 mmol). The mixture was stirred for 2 hours at 10° C. and then allowed to warm to ambient temperature and stirred for 24 hours. The mixture was poured into excess water and the precipitated solid collected by filtration. The solid was purified by trituration with a hot mixture of ethyl acetate (26 ml), hexane (2.6 ml) and triethylamine (0.1 ml) to give 5-(2-bromophenyl)-1-(4-nitrophenyl)-1H-tetrazole (C) (2.36 g; 73% yield) as an off-white solid, m.p. 169°–170° C.; NMR (d$_6$-acetone; 270 MHz): 7.61–7.86(m, 6H), 8.41(d, 2H); microanalysis, found: C, 44.8; H, 2.1; N, 20.0; Br, 23.6%; $C_{13}H_8BrN_5O_2$ requires: C, 45.1; H, 2.3; N, 20.2; Br, 23.1%.

(iii) A mixture of 4-methylphenyl boronic acid (9.7 g; 71 mmol), sodium carbonate (16.7 g; 158 mmol), water (100 ml), methanol (50 ml) and toluene (50 ml) was heated to 60° C. to give a clear solution. Compound C (20.0 g; 55 mmol) was then added, followed by tetrakis(triphenylphosphine)palladium (0.3 g; 0.25 mmol) and the mixture heated at reflux for 3 hours. Toluene (30 ml) was added and the warm mixture was filtered through diatomaceous earth. The organic phase was separated and the aqueous phase extracted with toluene (40 ml). The combined organic phases were evaporated to give a solid which was recrystallised from toluene/petroleum ether (100°–120° C.) (1:1 v/v) to give 5-(4'-methylbiphenyl-2-yl)-1-(4-nitrophenyl)-1H-tetrazole (D) (18.7 g; 90% yield), m.p. 164°–166° C.; NMR (CDCl$_3$): 2.3(3H, s), 6.45(2H, d), 6.85(4H, m), 7.38(1H, d), 7.65(2H, m), 7.85(1H, d), 8.0(2H, d).

(iv) A mixture of compound D (8.0 g; 21 mmol), N-bromosuccinimide (4.53 g; 25 mmol) and azo(bisisobutyronitrile) (73 mg) in methyl chloroform (50 ml) was heated at reflux for 4 hours. The mixture was cooled to ambient temperature, washed with water (3×50 ml), and the suspended solid collected by filtration to give 5-(4'-bromomethylbiphenyl-2-yl)-1-(4-nitrophenyl)-1H-tetrazole (E) (7.3 g), m.p. 192°–195° C.; NMR (CDCl$_3$): 4.4(2H, s), 6.52(2H, d), 6.85(2H, d), 7.07(2H, d), 7.4(1H, d), 7.7(2H, m), 7.9(1H, d).

(v) 4-amino-2,6-diethyl-3-iodopyridine (2 g) (obtained as described in Example 7 B) was added to a mixture of potassium t-butoxide (0.97 g) and 1,4,7,10,13,16-hexacyclooctadecane (200 mg) in THF (40 ml) and the mixture was stirred for 15 minutes. Compound E (4 g) was added and the mixture was stirred for 4 hours. Volatile material was removed by evaporation and the residue was dissolved in dichloromethane. The solution was washed with 0.1M citric acid solution and dried (MgSO$_4$). Solvent was removed by evaporation and the residue was purified by flash chromatography eluting with dichloromethane/methanol (12:1 v/v) to give 2,6-diethyl-3-iodo-4-[(2'-(1-(4-nitrophenyl)-1H-tetrazol-5-yl)biphenyl-4-yl)methylamino]pyridine (F) (0.9 g) as a solid; NMR (CDCl$_3$): 1.26(d of t, 6H), 2.70(q, 2H), 3.00(q, 2H), 4.35(d, 2H), 5.21(broad t, 1H), 6.10(s, 1H), 6.58(d, 2H), 6.79(d, 2H), 7.04(d, 2H), 7.37(m, 1H), 7.65(m, 2H), 7.86(d, 3H).

(v) Compound F (0.2 g) was added to a mixture of 4-methylphenylboronic acid (0.15 g) and tetrakis(triphenylphosphine)palladium (10 mg) in toluene (15 ml) and saturated sodium bicarbonate solution (4 ml). The solution was heated at reflux for 6 hours and then cooled to ambient temperature. The aqueous layer was separated and extracted with ethyl acetate (2×15 ml). The combined toluene and ethyl acetate solutions were dried (MgSO$_4$) and solvent removed by evaporation. The residue was purified by flash chromatography eluting with ethyl acetate to give 2,6-diethyl-3-(4-methylphenyl)-4-[(2'-(1-(4-nitrophenyl)-1H-tetrazol-5-yl)biphenyl-4-yl)methylamino]pyridine (A) (0.15 g) as a yellow foam; NMR (CDCl$_3$): 1.10(t, 3H), 1.27(t, 3H), 2.42(s, 3H), 2.50(q, 2H), 2.78(q, 2H), 4.19(s, 2H), 6.25(s, 1H), 6.50(d, 2H), 6.65(d, 2H), 6.90(d, 2H), 7.17(m, 3H), 7.34(m, 3H), 7.68(m, 3H), 7.86(m, 1H), 7.98(m, 1H); mass spectrum (+ve FAB, methanol/nitrobenzyl alcohol): 596(M+H)$^+$.

EXAMPLE 16

Using an analogous procedure to that described in Example 15 the following compound of formula I was obtained in 62% yield:

(Example 16): 2,6-diethyl-4-[(2'-(1H-tetrazol-5-yl)biphenyl-4-yl)methylamino]-3-[(4-trifluoromethyl)-phenyl]pyridine as a white solid, m.p. 224° C.; NMR (d$_6$-DMSO): 1.0(t, 3H), 1.18(t, 3H), 2.29(q, 2H), 2.67(q, 2H), 4.40(d, 2H), 6.59(s, 1H), 6.81(broad s, 1H), 7.10(dd, 4H), 7.40(m, 3H), 7.55(m, 3H), 7.93(d, 2H); mass spectrum (+ve FAB DMSO/nitrobenzyl alcohol): 528(M+H)$^+$.

The necessary starting material used in Example 16 corresponding to starting material A in Example 15 was obtained in 30% yield using an analogous procedure to that described in Example 15, part (vi), but starting from 4-(trifluoromethyl)phenylboronic acid as follows:

(Example 15A): 2,6-diethyl-4-[(2'-(1-(4-nitrophenyl)-1H-tetrazol-5-yl)biphenyl-4-yl)methylamino]-3-[(4-trifluoromethyl)phenyl]pyridine as a solid, m.p. 205° C.; NMR (CDCl$_3$): 1.11(t, 3H), 1.31(t, 3H), 2.47(q, 2H), 2.77(q, 2H), 4.11(broad t, 1H), 4.23(d, 2H), 6.26(s, 1H), 6.51(d, 2H), 6.70(d, 2H), 6.90(d, 2H), 7.33(m, 1H), 7.47(d, 2H), 7.75(m, 7H); mass spectrum (+ve FAB, DMSO/nitrobenzyl alcohol): 650(M+H)$^+$.

EXAMPLE 17

(Note: all parts by weight)

The compounds of the invention may be administered for therapeutic or prophylactic use to warm-blooded animals such as man in the form of conventional pharmaceutical compositions, typical examples of which include the following:

| a) | Capsule (for oral administration) | |
|---|---|---|
| | Active ingredient * | 20 |
| | Lactose powder | 578.5 |
| | Magnesium stearate | 1.5 |
| b) | Tablet (for oral administration) | |
| | Active ingredient * | 50 |
| | Microcrystalline cellulose | 400 |
| | Starch (pregelatinised) | 47.5 |
| | Magnesium stearate | 2.5 |
| c) | Injectable Solution (for intravenous administration) | |
| | Active ingredient * | 0.05–1.0 |
| | Propylene glycol | 5.0 |
| | Polyethylene glycol (300) | 3.0–5.0 |
| | Purified water | to 100% |
| d) | Injectable Suspension (for intramuscular administration) | |
| | Active ingredient * | 0.05–1.0 |
| | Methylcellulose | 0.5 |
| | Tween 80 | 0.05 |
| | Benzyl alcohol | 0.9 |
| | Benzalkonium chloride | 0.1 |

-continued

| Purified water | to 100% |

Note:
the active ingredient * may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae

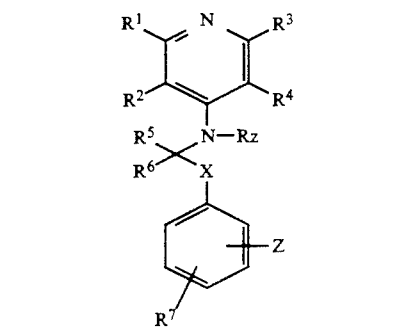

I

Ia

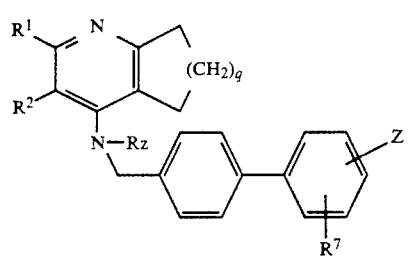

II

III

IV

Chemical Formulae

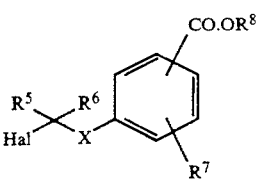

V

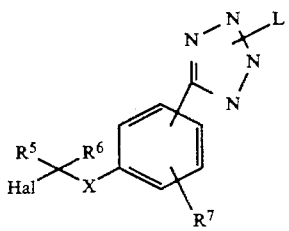

VI

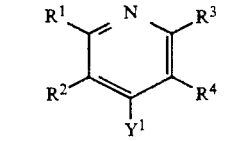

VII

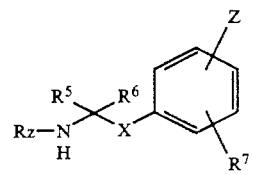

VIII

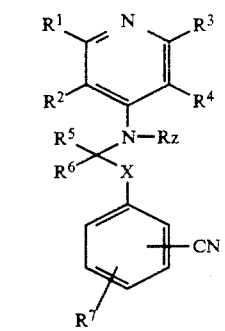

IX

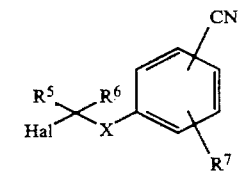

X

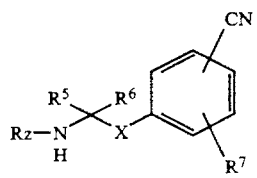

XI 5,236,937
33
-continued
Chemical Formulae
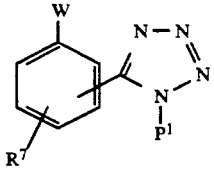
XII
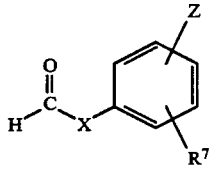
XIII
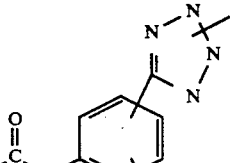
XIV
34
-continued
Chemical Formulae
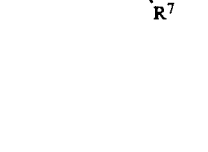
XV
XVI
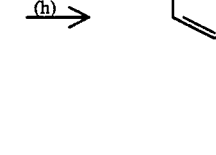
XVII
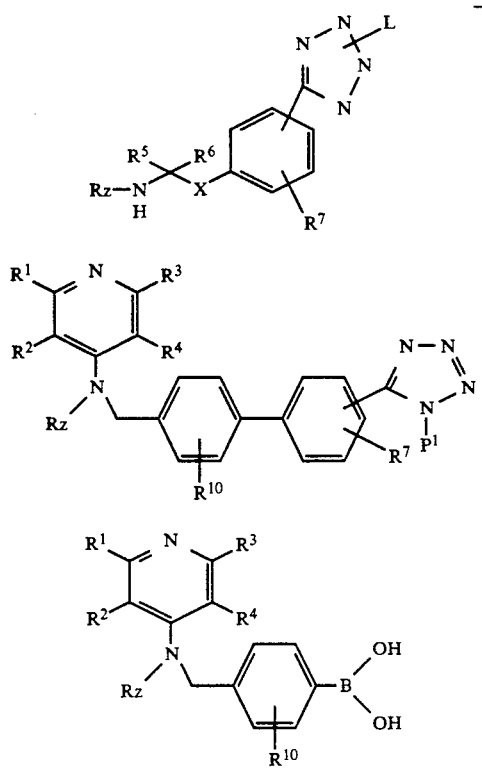
Scheme 1

-continued
Scheme 1

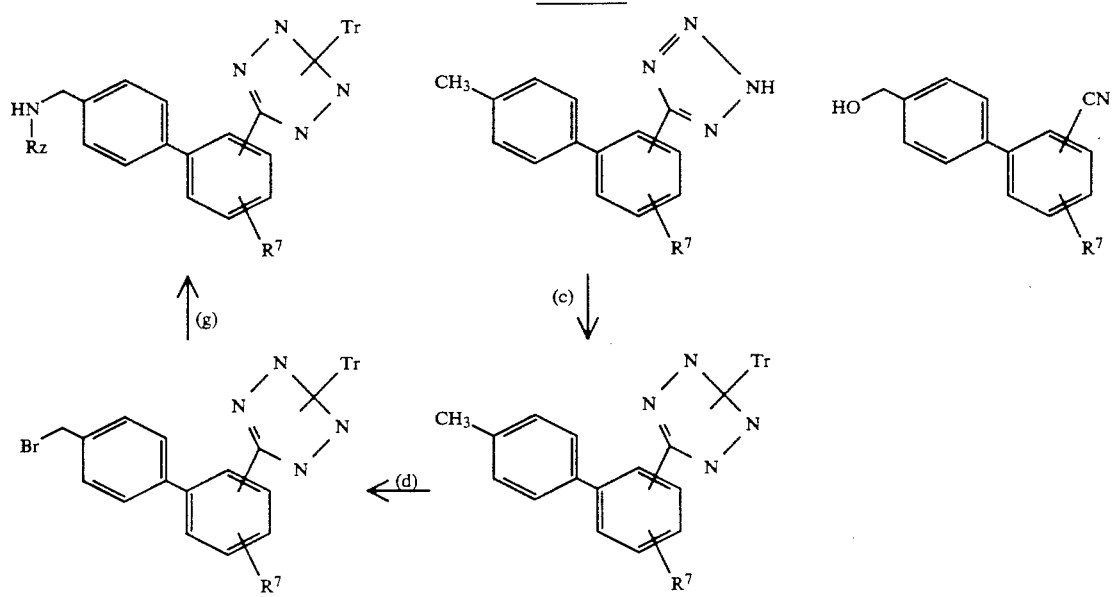

Note:
R = lower alkyl, benzyl, phenyl; Tr = triphenylmethyl (trityl) Rz = hydrogen or alkyl
Reagents:
a) BuLi/THF; ZnCl$_2$/Et$_2$O; Pd(Ph$_3$P)$_4$
b) Bu$_3$Sn.N$_3$/toluene; HCl/toluene
c) Tr.Cl/Et$_3$N/CH$_2$Cl$_2$
d) N-bromosuccinimide/azoisobutyronitrile/CCl$_4$
e) Potassium acetate, hexaoxacyclooctadecane, DME, reflux
f) Lithium borohydride, THF, 0–25° C.
g) Ammonia or alkylamine, ethanol, ambient temperature
h) 2-nitropropane, sodium ethoxide, reflux Scheme 2

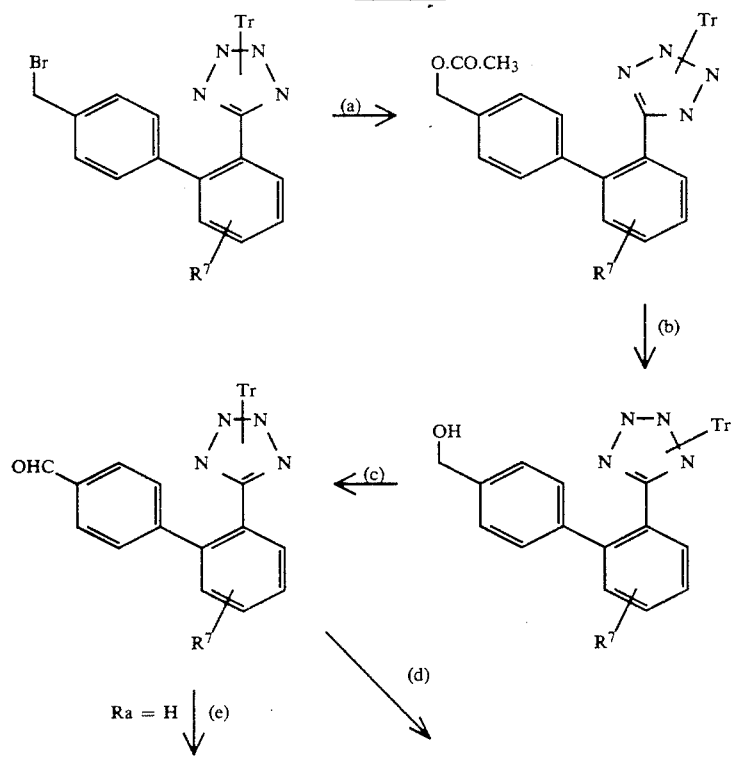

Scheme 2

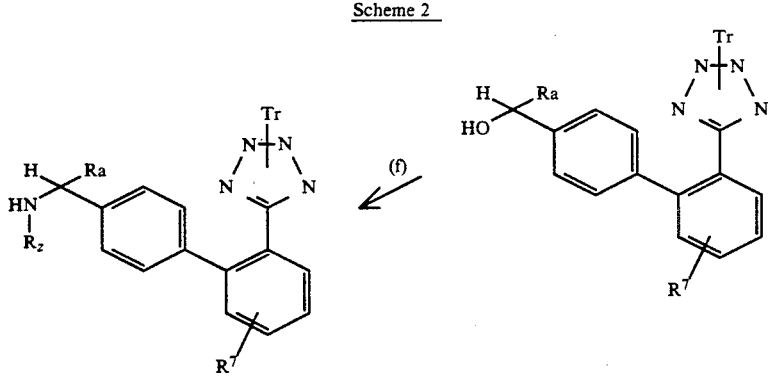

Note:
Tr = triphenylmethyl (trityl); Ra = (1–4C)alkyl
Rz = hydrogen or alkyl
Reagents:
(a) Potassium acetate, hexaoxacyclooctadecane, DME, reflux
(b) Lithium borohydride, THF, 0–25° C.
(c) Pyridine-SO₃ complex, Et₃N, DMSO, ambient temperature
(d) Ra.M, Et₂O/THF, −50° C. to ambient temperature
(e) NaBH₃CN, NH₄Cl
(f)(i) CH₃SO₂Cl, Et₃N, CH₂Cl₂
(ii) ammonia or alkylamine, ethanol

Scheme 3

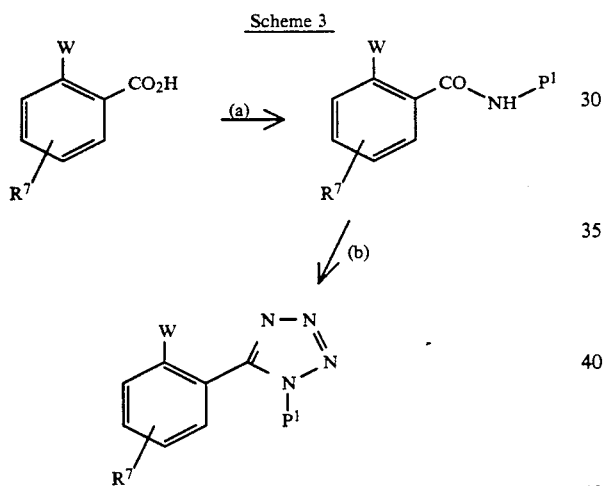

Reagents:
(a) thionyl chloride, DMF, toluene, 80° C.; then add to P¹.NH₂, toluene, NMP, ambient temperature
(b) (i) triethylamine, acetonitrile, DMF;
(ii) thionyl chloride, 10° C.; and
(iii) triethylamine, sodium azide, tetrabutylammonium bromide, 10° C. to ambient temperature

What we claim is:
1. A heterocyclic compound of the formula I

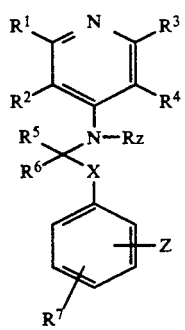

wherein $R^1$ is hydrogen, (1–8C)alkyl, (3–8C)cycloalkyl, phenyl or substituted (1–4C)alkyl, the latter containing one or more fluoro substituents or bearing a (3–8C)cycloalkyl, (1–4C)alkoxy or phenyl substituent;

$R^2$ is hydrogen, halogeno, (1–8C)alkyl, (3–8C)cycloalkyl, (3–8C)cycloalkyl-(1–4C)alkyl, carboxy, (1–4C)alkoxycarbonyl, (3–6C)alkenyloxycarbonyl, cyano, nitro, phenyl or phenyl(1–4C)alkyl;

$R^3$ is selected from halogeno, (1–4C)alkoxy, amino, alkylamino and dialkylamino of up to 6 carbon atoms, and any of the values defined for $R^1$;

$R^4$ is selected from hydrogen, (1–4C)alkyl optionally bearing an amino, hydroxy, (1–4C)alkoxy, carboxy or (1–4C)alkoxycarbonyl substituent or optionally containing one or more fluoro substituents, carboxy, (1–4C)alkoxycarbonyl, (3–6C)alkenyloxycarbonyl, cyano, nitro, carbamoyl, (1–4C)alkanoyl, N-alkylcarbamoyl and di-(N-alkyl)carbamoyl of up to 7 carbon atoms, formyl, halogeno, amino, alkylamino and dialkylamino of up to 6 carbon atoms, (1–4C)alkanoylamino, phenyl, phenyl(1–4-C)alkyl and benzoyl, the benzene ring of which last three groups optionally bearing one or two substituents independently selected from (1–4C)alkyl, (1–4C)alkoxy, halogeno, cyano, trifluoromethyl, nitro, hydroxy, carboxy, (1–4C)alkanoylamino, (1–4C)alkanoyl, fluoro(1–4C)alkoxy, hydroxy(1–4-C)alkyl, (1–4C)alkoxy(1–4C)alkyl, carbamoyl, alkyl or dialkylcarbamoyl of up to 7 carbon atoms, sulphamoyl, alkyl or dialkylsulphamoyl of up to 6 carbon atoms, (1–4C)alkoxycarbonyl, (1–4C)alkanesulphonamido, (1–4C)alkyl.S(O)$_n$-(in which n is zero, 1 or 2), phenyl, phenoxy, benzyloxy, benzyloxycarbonyl, benzamido and benzenesulphonamido, the benzene moiety of the last six groups optionally bearing a halogeno, (1–4C)alkyl or (1–4C)alkoxy substituent;

$R^5$ is hydrogen;
$R^6$ is hydrogen or (1–4C)alkyl;
$R^7$ is selected from hydrogen, (1–4C)alkyl, (1–4C)alkoxy, halogeno, trifluoromethyl, cyano and nitro;

39

X is phenylene optionally bearing a substituent selected from (1-4C)alkyl, (1-4C)alkoxy, halogeno, (1-4C)alkanoyl, trifluoromethyl, cyano and nitro;

Rz is hydrogen, (1-4C)alkyl, (1-4C)alkanoyl or benzoyl;

Z is 1H-tetrazol-5-yl, —CO.NH.(1H-tetrazol-5-yl) or a group of the formula —CO.OR$^8$ or —CO.NH.SO$_2$.R$^9$ in which R$^8$ is hydrogen or a non-toxic, biodegradable residue of a physiologically acceptable alcohol or phenol, and R$^9$ is (1-6C)alkyl, (3-8C)cycloalkyl or phenyl;

and wherein any of said phenyl moieties of R$^1$, R$^2$, R$^3$ or R$^9$ may be unsubstituted or bear one or two substituents independently selected from (1-4C)alkyl, (1-4C)alkoxy, halogeno, cyano and trifluoromethyl; or an N-oxide thereof; or a non-toxic salt thereof; but excluding ethyl 4-{{(3-amino-4-pyridyl)amino}methyl}benzoate, ethyl 4-{{(3-nitro-4-pyridyl)amino}methyl}benzoate, 2-{(4-pyridylamino)methyl}benzoic acid and 4-{(4-pyridylamino)methyl}benzoic acid.

2. A compound as claimed in claim 1 wherein

R$^1$ is hydrogen, methyl, ethyl, propyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl or 2-phenylethyl;

R$^2$ is hydrogen, halogeno, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentylethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, phenyl, benzyl, 1-phenylethyl or 2-phenylethyl;

R$^3$ is selected from hydrogen, methyl, ethyl, propyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl, 2-phenylethyl, fluoro, chloro, bromo, iodo, methoxy, ethoxy, amino, methylamino, ethylamino, butylamino, dimethylamino, diethylamino and dipropylamino;

R$^4$ is selected from hydrogen, methyl, ethyl, hydroxymethyl, 1-hydroxyethyl, 2-hydroxyethyl, aminomethyl, 2-aminoethyl, methoxymethyl, 2-methoxyethyl, 2-ethoxyethyl, carboxymethyl, 1-carboxyethyl, 2-carboxyethyl, methoxycarbonylmethyl, ethoxycarbonylmethyl, 2-methoxycarbonylethyl, 2-ethoxycarbonylethyl, fluoromethyl, trifluoromethyl, 2,2,2-trifluoroethyl, pentafluoroethyl, carboxy, methoxycarbonyl, ethoxycarbonyl, propoxycarbonyl, allyloxycarbonyl, 2-methyl-2-propenyloxycarbonyl, 3-methyl-3-butenyloxycarbonyl, cyano, nitro, carbamoyl, formyl, acetyl, butyryl, N-methylcarbamoyl, N-ethylcarbamoyl, N,N-dimethylcarbamoyl, N,N-diethylcarbamoyl, fluoro, chloro, bromo, iodo, amino, methylamino, ethylamino, butylamino, dimethylamino, diethylamino, dipropylamino, formamido, acetamido, propanamido, phenyl, benzyl, 1-phenylethyl, 2-phenylethyl and benzoyl, the benzene ring of which last five groups optionally bearing one or

40 two substituents independently selected from methyl, ethyl, methoxy, ethoxy, chloro, bromo, iodo, cyano, trifluoromethyl, nitro, hydroxy, carboxy, formamido, acetamido, propanamido, formyl, acetyl, butyryl, trifluoromethoxy, 2-fluoroethoxy, 2,2,2-trifluoroethoxy, 3,3,3-trifluoropropoxy, hydroxymethyl, 1-hydroxyethyl, 2-hydroxyethyl, 2-methoxyethyl, 2-ethoxyethyl, carbamoyl, N-methylcarbamoyl, N-ethylcarbamoyl, N,N-dimethylcarbamoyl, N,N-diethylcarbamoyl, sulphamoyl, N-methylsulphamoyl, N-ethylsulphamoyl, N,N-dimethylsulphamoyl, N,N-diethylsulphamoyl, methoxycarbonyl, ethoxycarbonyl, propoxycarbonyl, methanesulphonamido, ethanesulphonamido, methylthio, ethylthio, methylsulphinyl, ethylsulphinyl, methylsulphonyl, ethylsulphonyl, phenyl, phenoxy, benzyloxy, benzyloxycarbonyl, benzamido and benzenesulphonamido, the benzene moiety of the last six groups optionally bearing a fluoro, chloro, bromo, methyl, ethyl, methoxy or ethoxy substituent;

R$^6$ is hydrogen, methyl or ethyl;

R$^7$ is selected from hydrogen, methyl, ethyl, methoxy, ethoxy, fluoro, chloro, bromo, iodo, trifluoromethyl, cyano and nitro;

X is phenylene optionally bearing a substituent selected from methyl, ethyl, methoxy, ethoxy, fluoro, chloro, bromo, iodo, formyl, acetyl, propionyl, trifluoromethyl, cyano and nitro;

Rz is hydrogen, methyl, ethyl, formyl, acetyl, propionyl or benzoyl;

R$^8$ is hydrogen or a residue derived from a (1-6C)alkanol, or phenol or glycerol; and R$^9$ is methyl, ethyl, propyl, isopropyl, butyl, pentyl, cyclobutyl, cyclopentyl, cyclohexyl or phenyl;

and wherein any of said phenyl moieties of R$^1$, R$^2$, R$^3$ or R$^9$ may be unsubstituted or bear one or two substituents independently selected from methyl, ethyl, methoxy, ethoxy, fluoro, chloro, bromo, cyano and trifluoromethyl.

3. A compound as claimed in claim 1 wherein R$^4$ is selected from hydrogen, (1-4C)alkyl optionally bearing an amino, hydroxy or (1-4C)alkoxy substituent, carboxy, (1-4C)alkoxycarbonyl, (3-6C)alkenyloxycarbonyl, cyano, nitro, carbamoyl, (1-4C)alkanoyl, N-alkylcarbamoyl and di-(N-alkyl)carbamoyl of up to 7 carbon atoms, formyl, halogeno, amino, alkylamino and dialkylamino of up to 6 carbon atoms, (1-4C)alkanoylamino, phenyl, phenyl(1-4C)alkyl and benzoyl, the benzene ring of which last three groups optionally bearing one or two substituents independently selected from (1-4C)alkyl, (1-4C)alkoxy, halogeno, cyano, trifluoromethyl, nitro, hydroxy, carboxy, (1-4C)alkanoylamino, (1-4C)alkanoyl, fluoro(1-4C)alkoxy, hydroxy(1-4C)alkyl, (1-4C)alkoxy(1-4C)alkyl, carbamoyl, alkyl or dialkylcarbamoyl of up to 7 carbon atoms, sulphamoyl, alkyl or dialkylsulphamoyl of up to 6 carbon atoms, (1-4C)alkoxycarbonyl, (1-4C)alkanesulphonamido, (1-4C)alkyl.S(O)$_n$-(in which n is zero, 1 or 2), phenyl, phenoxy, benzyloxy, benzyloxycarbonyl, benzamido and benzenesulphonamido, the benzene moiety of the last six groups optionally bearing a halogeno, (1-4C)alkyl or (1-4C)alkoxy substituent; and Rz is hydrogen.

4. A compound as claimed in claim 1 wherein R$^1$ is (1-4C)alkyl; R$^2$ is hydrogen, halogeno or (1-4C)alkoxycarbonyl; R$^3$ is (1-4C)alkyl; R$^4$ is hydrogen, halogeno, (1-4C)alkoxycarbonyl, benzoyl or phenyl, the benzene ring of which last two groups optionally bearing one or two substituents independently selected from (1–4C)alkyl, (1–4C)alkoxy, halogeno, cyano, trifluoromethyl and nitro; $R^5$, $R^6$ and Rz are each hydrogen; X is p-phenylene; and Z is carboxy or 1H-tetrazol-5-yl and is attached at the ortho position relative to X; or a non-toxic salt thereof.

5. A compound as claimed in claim 1 wherein $R^4$ is (1–4C)alkoxycarbonyl or halogeno; $R^6$ is hydrogen, X is p-phenylene and Z is 1H-tetrazol-5-yl.

6. A compound as claimed in claim 1 selected from:
2,6-dimethyl-3-iodo-4-[(2'-(1H-tetrazol-5-yl)bipheny-4-yl)methylamino]pyridine;
3-chloro-2,6-dimethyl-4-[(2'-(1H-tetrazol-5-yl)biphenyl-4yl)methylamino]pyridine;
2,6-Diethyl-3-iodo-4-[(2'-(1H-tetrazol-5-yl)biphenyl-4-yl)methylamino]pyridine;
3-chloro-2,6-diethyl-4-[(2'-(1H-tetrazol-5-yl)biphenyl-4-yl)methylamino]pyridine; and
3-bromo-2,6-diethyl-4-[(2'-(1H-tetrazol-5-yl)biphenyl-4-yl)methylamino]pyridine; and the non-toxic salts thereof.

7. A salt as claimed in claim 1 which is selected from the group consisting of salts with acids forming physiologically acceptable anions and, for those compounds of formula I which are acidic, alkali metal, alkaline earth metal, aluminium and ammonium salts, and salts with organic bases affording physiologically acceptable cations.

8. A pharmaceutical composition which comprises a compound of the formula I, or a non-toxic salt thereof, as claimed in claim 1, together with a pharmaceutically acceptable diluent or carrier.

9. A method for antagonising one or more of the actions of angiotensin II in a warm-blooded animal requiring such treatment which comprises administering to said animal an antagonistically effective amount of a compound of formula I, or a non-toxic salt thereof, as defined in claim 1.

10. A compound of the formula III

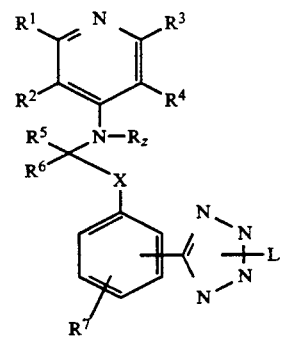

wherein $R^1$, $R^2$, $R^3$, $R^4$, $R^5$, $R^6$, $R^7$, Rz and X have any of the meanings defined in claim 1, and L is a protecting group.

11. A compound of the formula XIII

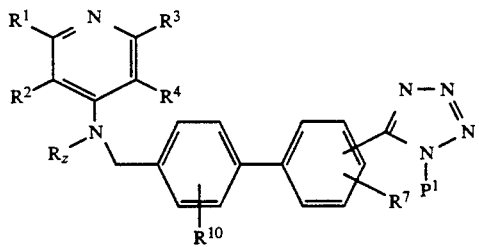

wherein $R^1$, $R^2$, $R^3$, $R^4$, $R^7$ and Rz have any of the meanings defined in claim 1; $R^{10}$ is hydrogen, (1–4C)alkyl, (1–4C)alkoxy, halogeno, trifluoromethyl, cyano or nitro; and $P^1$ is an electron-deficient phenyl group or is a pyridyl or pyrimidyl group.

* * * * *